(12) United States Patent
Lewis et al.

(10) Patent No.: US 7,737,112 B2
(45) Date of Patent: Jun. 15, 2010

(54) COMPOSITION FOR ENZYME INHIBITION

(75) Inventors: Evan R. Lewis, Pacifica, CA (US); Mark Nguyen Ho, San Jose, CA (US); Fabiana N. Fonseca, New York, NY (US)

(73) Assignee: Onyx Therapeutics, Inc., South San Francisco, CA (US)

( * ) Notice: Subject to any disclaimer, the term of this patent is extended or adjusted under 35 U.S.C. 154(b) by 742 days.

(21) Appl. No.: 11/299,265

(22) Filed: Dec. 7, 2005

(65) Prior Publication Data

US 2006/0128611 A1  Jun. 15, 2006

Related U.S. Application Data

(60) Provisional application No. 60/634,366, filed on Dec. 7, 2004, provisional application No. 60/655,930, filed on Feb. 23, 2005.

(51) Int. Cl.
*A61K 38/02* (2006.01)
*C08B 37/16* (2006.01)

(52) U.S. Cl. ............................. 514/2; 514/17; 514/18; 514/58; 536/46; 536/103; 536/112

(58) Field of Classification Search ................ 536/1.11, 536/46, 58, 103, 112; 514/17, 18
See application file for complete search history.

(56) References Cited

U.S. PATENT DOCUMENTS

| | | | |
|---|---|---|---|
| 5,134,127 A | | 7/1992 | Stella et al. |
| 5,135,919 A | * | 8/1992 | Folkman et al. ............... 514/56 |
| 5,376,645 A | | 12/1994 | Stella et al. |
| 5,441,944 A | * | 8/1995 | Weisz et al. .................. 514/58 |
| 5,874,418 A | | 2/1999 | Stella et al. |
| 6,046,177 A | | 4/2000 | Stella et al. |
| 6,133,248 A | | 10/2000 | Stella |
| 6,831,099 B1 | | 12/2004 | Crews et al. |
| 2003/0236223 A1 | * | 12/2003 | Wagner et al. ................ 514/58 |
| 2005/0101781 A1 | * | 5/2005 | Agoulnik et al. ............ 546/148 |

FOREIGN PATENT DOCUMENTS

| | | |
|---|---|---|
| WO | WO-01/28579 A2 | 4/2001 |
| WO | WO-2005/105827 A2 | 11/2005 |
| WO | WO-2005/111008 A2 | 11/2005 |
| WO | WO-2006/017842 A | 2/2006 |

OTHER PUBLICATIONS

Meng (Cancer Research 59, 2798, 1999).*
Elofsson et al., "Towards subunit-specific proteasome inhibitors: synthesis and evaluation of peptide α', β'-epoxyketones", *Chemistry & Biology*, 6:811-822 (1999).
Loftsson et al., "Pharmaceutical Applications of Cyclodextrins. 1. Drug Solubilization and Stabilization," *Journal of Pharmaceutical Sciences, American Pharmaceutical Association*, 85(10):1017-1025 (1996).
Myung et al., "Lack of Proteasome Active Site Allostery as Revealed by Subunit-Specific Inhibitors," *Molecular Cell*, 7(2):411-420 (2001).
Sin et al., "Total synthesis of the potent proteasome inhibitor epoxomicin: a useful tool for understanding proteasome biology", *Bioorganic & Medicinal Chemistry Letters*, 9:2283-2288 (1999).
Thompson D.O., "Cyclodextrins-enabling excipients: their present and future use in pharmaceuticals," *Critical Reviews in Therapeutic Drug Carrier Systems*, 14(1):1-104 (1997).
Strickley, Robert G., "Solubilizing Excipients in Oral and Injectable Formulations," *Pharmaceutical Research*, 21(2):201-230 (2004).
Tong, Wei-Qin (Tony), "Applications of Complexation in the Formulation of Insoluble Compounds," R. Liu, Ed., pp. 111-139 (2000).

* cited by examiner

*Primary Examiner*—David Lukton
(74) *Attorney, Agent, or Firm*—Ropes & Gray LLP

(57) ABSTRACT

Compositions comprising one or more practically insoluble proteasome inhibitors and a cyclodextrin, particularly a substituted cyclodextrin, substantially increase the solubility of these proteasome inhibitors and facilitate their administration. Such compositions optionally comprise a buffer. Methods of treatment using such compositions are also disclosed.

32 Claims, 2 Drawing Sheets

COMPOSITION FOR ENZYME INHIBITION

CROSS-REFERENCE TO RELATED APPLICATIONS

This application claims the benefit of U.S. Provisional Application No. 60/634,366, filed Dec. 7, 2004, and U.S. Provisional Application No. 60/655,930 filed Feb. 23, 2005, the specifications of which are hereby incorporated by reference in their entirety.

BACKGROUND OF THE INVENTION

The proteasome has been validated as a therapeutic target, as demonstrated by the recent FDA approval of bortezomib, a boronic acid proteasome inhibitor, for the treatment of multiple myeloma. However, other more highly proteasome-specific inhibitors that could have fewer toxic side effects have recently been described. These compounds include peptide epoxy ketones such as epoxomicin and peptide (b), described in U.S. Pat. No. 6,831,099, the contents of which are hereby incorporated by reference, and peptide (a), described in U.S. Provisional Application No. 60/569,096, filed May 7, 2004, the contents of which are hereby incorporated by reference. However, the low aqueous solubility of some of these compounds makes it difficult to formulate compositions with optimal bioavailability. Thus, additional methods of formulating peptide epoxy ketones are needed.

SUMMARY OF THE INVENTION

It has now been found that the solubility of proteasome inhibitors, such as the peptide epoxy ketones peptide (a) and peptide (b) (structures or definitions for these peptides are provided in Group 3 and Group 1, respectively), is significantly enhanced when formulated with a cyclodextrin.

In one embodiment, the present invention is a pharmaceutical composition that includes a practically insoluble proteasome inhibitor, a cyclodextrin and optionally a buffer. Such pharmaceutical compositions typically include a pharmaceutically effective amount of the proteasome inhibitor, e.g., which ameliorates the effects of neurodegenerative disease (such as Alzheimer's disease), immunological conditions, muscle-wasting diseases, cancer, chronic infectious diseases, fever, muscle disease, denervation, nerve injury, and/or fasting, among others, when administered to a patient.

In another aspect, the invention provides anti-inflammatory compositions that include a therapeutically effect amount of a proteasome inhibitor, a cyclodextrin and optionally a buffer.

In another aspect, the invention provides methods that involve administering to or contacting a subject, a cell, a tissue, an organ or an organism with an effective amount of a composition comprising one or more proteasome inhibitors disclosed herein. These methods include, but are not limited to, inhibiting or reducing HIV infection in a subject; affecting the level of viral gene expression in a subject; altering the variety of antigenic peptides produced by the proteasome in an organism; determining whether a cellular, developmental, or physiological process or output in an organism is regulated by the proteolytic activity of a particular Ntn hydrolase; treating Alzheimer's disease in a subject; reducing the rate of muscle protein degradation in a cell; reducing the rate of intracellular protein degradation in a cell; reducing the rate of p53 protein degradation in a cell; inhibiting the growth of p53-related cancers in a subject; inhibiting antigen presentation in a cell; suppressing the immune system of a subject (e.g., conditions such as septic shock, psoriasis, graft rejection, and rheumatoid arthritis); inhibiting IκB-α degradation in an organism; reducing the content of NF-κB in a cell, muscle, organ or subject; affecting cyclin-dependent eukaryotic cell cycles; treating proliferative disease in a subject; affecting proteasome-dependent regulation of oncoproteins in a cell; treating cancer growth in a subject; treating p53-related apoptosis in a subject; and screening proteins processed by N-terminal nucleophile hydrolases in a cell.

The invention, in another aspect, is directed to medical devices that include a pharmaceutical composition disclosed herein.

Other features and advantages of the invention will be apparent from the following detailed description and from the claims.

DETAILED DESCRIPTION

Pharmaceutical compositions of the invention include a practically insoluble proteasome inhibitor, a cyclodextrin and optionally a buffer.

Figure 1:
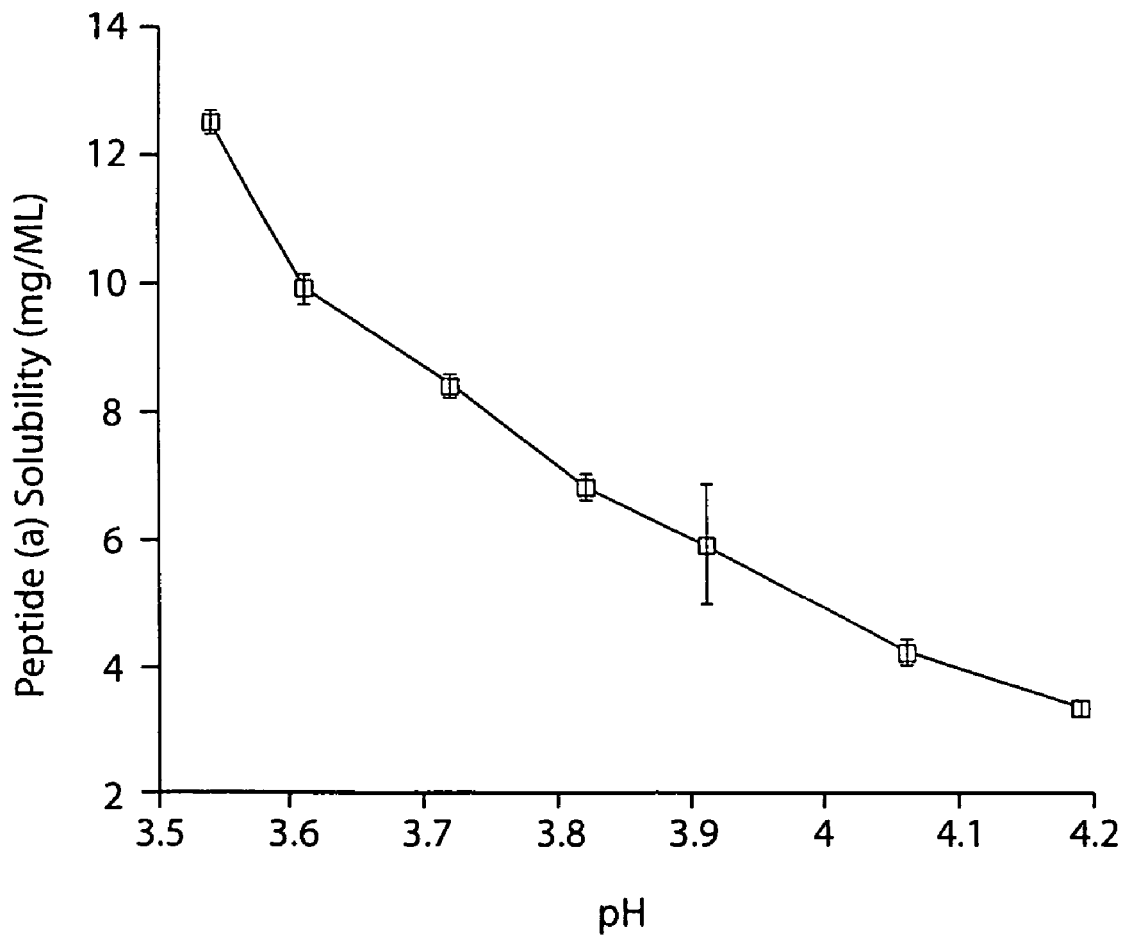
FIG. 1 shows the solubility of peptide (a) at various pH values in aqueous 10% (w/v) sulfobutyl ether beta-cyclodextrin (SBECD)/10 mM sodium citrate solutions.

The amount of proteasome inhibitor that can be solubilized is dependent on several parameters. One such parameter is pH. As shown in FIG. 1, higher pH results in poorer solubility of a basic compound, and lower pH would be expected to decrease solubility of an acidic compound, as is well known in the art. However, a pH should be selected to provide suitable stability of the proteasome inhibitor. For example, lower pH results in decreased chemical stability of one such compound, as demonstrated in FIG. 2. The effects of pH on a compound's stability and solubility can be readily determined using methods widely known in the art and disclosed herein. For formulations to be administered to a mammal, the pH is preferably from pH 2.5 to pH 9.

In many compositions of the invention, the primary source of pH control is the buffer. Typically, the buffer is present as an acid or a base and its conjugate base or acid, respectively. In one embodiment, the range of buffering salt is 1-100 mM, preferably between 5-50 mM, most preferentially about 10 mM (in solid formulations, the amount of buffer is selected to produce this concentration after reconstitution/dilution). The concentration of buffer and the pH of the solution are advantageously chosen to give optimal balance of solubility and stability.

Examples of suitable buffers include mixtures of weak acids and alkali metal salts (e.g., sodium, potassium) of the conjugate base of weak acids such as sodium tartrate and sodium citrate. The preferred buffer is sodium citrate/citric acid.

Cyclodextrins of the invention include alpha-, beta- and gamma-cyclodextrin. In one embodiment, the cyclodextrin is either a substituted or non-substituted β-cyclodextrin, present, for example, at from 5-20% (w/v). In a certain embodiment, the preferred amount of a cyclodextrin is about 10% (w/v). In another preferred embodiment, the cyclodextrin is a substituted β-cyclodextrin. Substituted cyclodextrins increase the solubility of the cyclodextrin and mitigate toxic effects associated with unsubstituted cyclodextrins.

Examples of substituted β-cyclodextrins include those substituted with one or more hydrophilic groups, such as monosaccharide (e.g., glucosyl, maltosyl), carboxyalkyl (e.g., carboxylmethyl, carboxyethyl), hydroxyalkyl-substituted (e.g., hydroxyethyl, 2-hydroxypropyl) and sulfoalkylether-substituted beta-cyclodextrin. Particularly suitable beta-cyclodextrins include hydroxypropyl beta-cyclodextrin (HPBCD) and sulfobutylether beta-cyclodextrin (SBECD), preferentially SBECD. However, it is understood that typically any substitution to the cyclodextrin, including substitution by hydrophobic groups such as alkyls, will improve its aqueous solubility by disrupting the hydrogen-bonding network within the crystal lattice of the solid cyclodextrin, thereby lowering the lattice energy of the solid. The degree of substitution is not believed to be critical; however, the degree of substitution is advantageously at least 1% and typically 2% to 10%, such as 3% to 6%.

One particular embodiment of this invention is a pharmaceutical formulation comprising 1 to 5 mg/ml of a proteasome inhibitor, 5% to 25% (w/v) of a cyclodextrin such as HPBCD or SBECD and 5 mM to 20 mM of a buffer producing a pH of about pH 3 to about pH 6, e.g., a solution of 2 mg/ml of a proteasome inhibitor (peptide (a)), 10% (w/v) SBECD, 10 mM sodium citrate, pH 3.5.

Proteasome Inhibitors

Suitable proteasome inhibitors, particularly those with epoxide and aziridine moieties, are described in U.S. Pat. No. 6,831,099 and U.S. Provisional Application Nos. 60/562,340, filed Apr. 15, 2004, 60/569,096, filed May 7, 2004, 60/596, 885, filed May 10, 2004, 60/572,072, filed May 17, 2004, 60/599,401, Aug. 6, 2004, 60/610,001, filed Sep. 14, 2004, 60/610,002, filed Sep. 14, 2004, 60/610,040, Sep. 14, 2004, 60/610,159, filed Sep. 14, 2004, 60/620,573, filed Oct. 20, 2004, and 60/634,366, filed Dec. 7, 2004, the contents of which are incorporated herein by reference.

In each of the following groups, the values for various moieties (e.g., for $R^1$, etc.) are understood to be consistent within a group, but values for one group (e.g., Group 1) do not apply to another group (Group 9).

Group 1

In one embodiment, the proteasome inhibitor is an epoxide- or aziridine-containing compound, which preferably contains groups proximate to the heteroatom-containing, three-membered rings, such that a ring-opening reaction of the heteroatom-containing three-membered ring is facilitated. Such groups include electron-withdrawing groups (E.W.G.) adjacent to (for example, at a carbon vicinal to a carbon atom of the three-membered, heteroatom-containing ring), or in electronic communication with (for example, via a carbon atom, or an alkenyl or alkynyl linkage), epoxide or aziridine functionalities. The E.W.G. can be bonded to one of the carbon atoms of the heteroatom-containing, three-membered ring. E.W.G. include, for example, cyano, isocyano, nitro, amide, sulfonyl, β-carboxy vinyl, sulfinyl, β,β-dicyano vinyl, formyl, carboxyl, alkyloxy- and aryloxy-carbonyl, 1-tetrazolyl, carbamoyl, sulfamoyl, carbonyl, sulfoxide groups, and halogenated or dihalogenated carbon atoms such as —CHX—, —CXX'—, and —CRX— (where X and X' are independently selected halogens, and R is a carbon-containing substituent such as alkyl, aryl alkenyl, alkynyl and the like). In some preferred embodiments, E.W.G. is a carbonyl group.

In some embodiments, it may be desirable to utilize E.W.G. that are of size, charge, and polarity sufficient to interact electronically with particular polar or charged moieties within an Ntn hydrolase. For example, an ionized aspartate or glutamate side chain can be present in the Ntn, and interact with, and stabilize, an electron-withdrawing group present in a peptide epoxide. Such groups act as an "anion hole," with which E.W.G. can interact when enzyme inhibitors are bound to Ntn, resulting in increased electrophilicity of E.W.G.

Some peptide epoxide or peptide aziridine compounds have a ketone functionality as the electron-withdrawing group, along with epoxide or aziridine functional groups. Particular examples are peptide α',β'-epoxy ketones or peptide α',β'-aziridine ketones, in which the carbon atoms forming two of the three members of the epoxide or aziridine ring are one (α') and two (β') carbons from the ketone, and the ketone carbon is bonded to one of the carbon atoms of the heteroatom-containing, three-membered ring. Further groups can be bonded to α' or β' carbons such as hydrogen and $C_{1-4}$alkyl groups, including methyl, ethyl, propyl and butyl groups. Groups bonded to α' or β' carbons can be further substituted with hydroxy, halogen, amino, carboxy, carbonyl, thio, sulfide, ester, amide or ether functionality.

For example, a carboxylic acid group can be bonded directly to the α' carbon, or via a linker. The linker can be $C_{1-4}$ alkylene, $C_{2-5}$ alkenylene, $C_{2-5}$ alkynylene, aryl, oxygen, sulfur, or amine. This carboxylic acid can be part of a peptide moiety extending from the α carbon of the heteroatom-containing, three-membered ring. In this way, peptides containing side chains can be constructed. Such side chains can be labeled as P1', P2', and so forth, with P1' being the first side chain adjacent to the α' carbon, P2' being the second, and so forth. Optimization of side chains for P1', P2' and other positions can result in enzyme inhibitors with desirable specificity, or desirable inhibition rates. Side chains for P1', P2' and so forth can be any of those side chains discussed herein.

In embodiments including such groups bonded to α' carbons, the stereochemistry of the α'-carbon (that carbon forming a part of the epoxide or aziridine ring) can be (R) or (S). The invention is based, in part, on the structure-function information disclosed herein, which suggests the following preferred stereochemical relationships. Note that a preferred compound may have a number of stereocenters having the indicated up-down (or β-α, where β as drawn herein is above the plane of the page) or (R)-(S) relationship (that is, it is not required that every stereocenter in the compound conform to the preferences stated). In some preferred embodiments, the stereochemistry of the α' carbon is (R), that is, the X atom is β, or above the plane of the molecule, when drawn as below. For example, the following general structural formula (I) demonstrates a preferred stereochemistry for some embodiments:

$$\text{peptide-E.W.G.} \overset{H_2C}{\underset{R}{\diagdown}} X \quad \quad I$$

where X is oxygen or an NH or N-alkyl group, E.W.G. is an electron withdrawing group as described above, "peptide" is a peptide as describe below, and R is a hydrogen atom, a $C_{1-4}$ alkyl group, which can be further substituted with hydroxy, halogen, amino, carboxy, carbonyl, thio, sulfide, ester, amide or ether functionality. For some embodiments, the X atom should be configured as above in order to facilitate interaction with an N-terminal nucleophilic group in an Ntn hydrolase. For example, irreversible interactions of enzyme inhibitors with the β5/Pre2 subunit of 20S proteasome which lead to inhibition appear to be facilitated by the configuration illustrated above. In the case of other Ntn hydrolases, the opposite stereochemistry of the α-carbon of the peptide epoxides or peptide aziridines may be preferred.

In the case illustrated above, the β' carbon is substituted with two hydrogen atoms. Regarding the stereochemistry, the chiral α' carbon is indicated with a star, and the Cahn-Ingold-Prelog rules for determining absolute stereochemistry are followed. These rules are described, for example, in Organic Chemistry, Fox and Whitesell; Jones and Bartlett Publishers, Boston, Mass. (1994); Section 5-6, pp 177-178, which section is hereby incorporated by reference. The stereochemistry of the α' carbon is (R) when the oxygen or nitrogen has the highest priority, the peptide-E.W.G. group has second highest priority, and the —CH$_2$—X— group has third highest priority. If the relative priorities of the peptide-E.W.G., —CH$_2$—X—, and R groups change, the nominal stereochemistry can change, but the essential configuration of the groups can remain the same, for some preferred embodiments. That is, referring to the general structure immediately above, peptide-E.W.G. is joined to the chiral α' carbon from the left, R is joined to the chiral α' carbon from the right, and the X atom(s) project(s) from the plane of the page. The nitrogen atom of an aziridine ring can also, in principle, be chiral, as discussed in March, Advanced Organic Chemistry, 4$^{th}$ Ed. (1992) Wiley-Interscience, New York, pp. 98-100, which pages are incorporated herein by reference.

The peptide epoxides or peptide aziridines also include a peptide moiety. The peptide moiety is bonded to the electron-withdrawing group. The bond is made between the electron-withdrawing group and any portion of the peptide. For example, in some preferred embodiments, the E.W.G. is bonded to the terminal backbone unit, such as for example, to the carboxy terminus of the peptide. Alternatively, the E.W.G. can be bonded to the amino terminus of the peptide. In other embodiments, the E.W.G. can be bonded to a side chain of the peptide moiety.

Peptides can have a repeating backbone structure with side chains extending from the backbone units. Generally, each backbone unit has a side chain associated with it, although in some cases, the side chain is a hydrogen atom. In other embodiments, not every backbone unit has an associated side chain. Peptides useful in peptide epoxides or peptide aziridines have two or more backbone units. In some embodiments useful for inhibiting chymotrypsin-like (CT-L) activity of the proteasome, between four and eight backbone units are present, and in some preferred embodiments for CT-L inhibition, between four and six backbone units are present. In other embodiments useful for inhibiting the PGPH activity of the proteasome, between two and eight backbone units are present, and in some preferred embodiments for PGPH inhibition, between three and six backbone units are present.

The side chains extending from the backbone units can include natural aliphatic or aromatic amino acid side chains, such as hydrogen (glycine), methyl (alanine), iso-propyl (valine), sec-butyl (isoleucine), iso-butyl (leucine), phenylmethyl (phenylalanine), and the side chain constituting the amino acid proline. The side chains can also be other aliphatic or aromatic groups such as ethyl, n-propyl, n-butyl, t-butyl, and aryl substituted derivatives such as 1-phenylethyl, 2-phenylethyl, (1-naphthyl)-methyl, (2-naphthyl)-methyl, 1-(1-naphthyl)ethyl, 1-(2-naphthyl)ethyl, 2-(1-naphthyl)ethyl, 2-(2-naphthyl)ethyl, and similar compounds. The aryl groups can be further substituted with C$_{1-6}$alkyl groups, or substituted alkyl groups, such as acetyl and the like, or further aryl groups, or substituted aryl groups, such as benzoyl and the like. Heteroaryl and/or heterocyclyl groups can also be used as side chain substituents. Heteroaryl groups include nitrogen-, oxygen-, and sulfur-containing aryl groups such as thienyl, benzothienyl, naphthothienyl, thianthrenyl, furyl, pyranyl, isobenzofuranyl, chromenyl, pyrrolyl, imidazolyl, pyrazolyl, pyridyl, pyrazinyl, indolyl, purinyl, quinolyl, and the like. Heterocyclyl groups include piperidine, piperazine, pyrrolidine, morpholine, tetrahydrofuran, lactones, lactams, and the like.

In some embodiments, polar or charged residues can be introduced into the peptide epoxides or peptide aziridines. For example, naturally occurring amino acids such as hydroxy-containing (Thr, Tyr, Ser) or sulfur-containing (Met, Cys) can be introduced, as well as non-essential amino acids, for example taurine, carnitine, citrulline, cystine, ornithine, norleucine and others. Non-naturally occurring side chain substituents with charged or polar moieties can also be included, such as, for example, C$_1$-C$_6$ alkyl chains or C$_6$-C$_{12}$ aryl groups with one or more hydroxy, short chain alkoxy, sulfide, thio, carboxyl, ester, phospho, amido or amino groups, or such substituents substituted with one or more halogen atoms. In some preferred embodiments, there is at least one aryl group present in a side chain of the peptide moiety.

In some embodiments, the backbone units are amide units [—NH—CHR—C(=O)—], in which R is the side chain. Such a designation does not exclude the naturally occurring amino acid proline, or other non-naturally occurring cyclic secondary amino acids, which will be recognized by those of skill in the art.

In other embodiments, the backbone units are N-alkylated amide units (for example, N-methyl and the like), olefinic analogs (in which one or more amide bonds are replaced by olefinic bonds), tetrazole analogs (in which a tetrazole ring imposes a cis-configuration on the backbone), or combinations of such backbone linkages. In still other embodiments, the amino acid α-carbon is modified by α-alkyl substitution, for example, aminoisobutyric acid. In some further embodiments, side chains are locally modified, for example, by Δ$^E$ or Δ$^Z$ dehydro modification, in which a double bond is present between the α and β atoms of the side chain, or for example by Δ$^E$ or Δ$^Z$ cyclopropyl modification, in which a cyclopropyl group is present between the α and β atoms of the side chain. In still further embodiments employing amino acid groups, D-amino acids can be used. Further embodiments can include side chain-to-backbone cyclization, disulfide bond formation, lactam formation, azo linkage, and other modifications discussed in "Peptides and Mimics, Design of Conformationally Constrained" by Hruby and Boteju, in "Molecular Biology and Biotechnology: A Comprehensive Desk Reference", ed. Robert A. Meyers, VCH Publishers (1995), pp. 658-664, which is hereby incorporated by reference.

The enzyme inhibitors for inhibition of chymotrypsin-like (CT-L) activity of Ntn include at least four backbone units. In some particularly preferred CT-L inhibitor embodiments, at least four amide units and an α',β'-epoxy ketone or α',β'-aziridine ketone moiety are present (tetrapeptide epoxy ketones or tetrapeptide aziridine ketones). In particular CT-L inhibitor embodiments with at least four amide units, the peptide moiety, and the ketone and epoxide or aziridine functionalities of the enzyme inhibitors form compounds with structural formula (II):

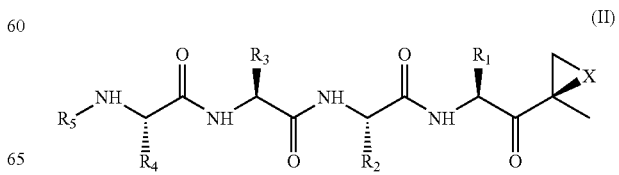

(II)

where X is oxygen, NH, or N-alkyl, $R_1$, $R_2$, $R_3$, and $R_4$ are independently selected from $C_{1-6}$alkyl, $C_{1-6}$hydroxyalkyl, $C_{1-6}$alkoxyalkyl, aryl, heteroaryl, $C_{1-6}$heteroaralkyl, heterocyclyl, $C_{1-6}$heterocycloalkyl, and aryl-substituted $C_{1-6}$alkyl, wherein such groups can further include: amide linkages; amines; carboxylic acids and salts thereof; carboxyl esters, including $C_{1-5}$alkyl esters and aryl esters; thiols and thioethers; and $R_5$ is a further chain of amino acids, hydrogen, acetyl, or a protecting group, such as N-terminal protecting groups known in the art of peptide synthesis, including t-butoxy carbonyl (BOC), benzoyl (Bz), fluoren-9-ylmethoxycarbonyl (Fmoc), triphenylmethyl(trityl) and trichloroethoxycarbonxyl (Troc) and the like. The use of various N-protecting groups, e.g., the benzyloxy carbonyl group or the t-butyloxycarbonyl group (BOC), various coupling reagents, e.g., dicyclohexylcarbodiimide, 1,3-diisopropylcarbodiimide (DIC), 1-(3-dimethylaminopropyl)-3-ethylcarbodiimide (EDC), N-hydroxyazabenzotriazole (HATU), carbonyldiimidazole, or 1-hydroxybenzotriazole monohydrate (HBT), and various cleavage reagents: for example, trifluoroacetic acid; HCl in dioxane; hydrogenation on Pd—C in organic solvents, such as methanol or ethyl acetate; boron tris(trifluoroacetate); and cyanogen bromide, and reaction in solution with isolation and purification of intermediates is well-known classical peptide methodology.

In some embodiments of chymotrypsin-like activity inhibitors, $R_1$ is $C_{1-6}$alkyl. In some embodiments of chymotrypsin-like activity inhibitors, $R_1$ is isobutyl. In some embodiments of chymotrypsin-like activity inhibitors, $R_2$ is $C_{1-6}$alkyl or aryl. In some embodiments of chymotrypsin-like activity inhibitors, $R_2$ is phenyl, phenylmethyl, or 1-naphthyl. In some embodiments of chymotrypsin-like activity inhibitors, $R_3$ is $C_{1-6}$alkyl or aryl. In some embodiments of chymotrypsin-like activity inhibitors, $R_3$ is isobutyl, phenyl or 1-naphthyl. In some embodiments of chymotrypsin-like activity inhibitors, $R_4$ is $C_{1-6}$alkyl, aryl, and aryl-substituted $C_{1-6}$alkyl. In some embodiments of chymotrypsin-like activity inhibitors, $R_4$ is isobutyl, phenyl, 1-naphthyl, phenylmethyl, or 2-phenylethyl. In some embodiments of chymotrypsin-like activity inhibitors, $R_5$ is hydrogen, $C_{1-6}$ alkanoyl, aryl, heteroaryl, where substituents include halogen, carbonyl, nitro, hydroxy, aryl, and $C_{1-5}$ alkyl. In some embodiments of chymotrypsin-like activity inhibitors, $R_5$ is hydrogen, acetyl, aryl.

In some preferred embodiments of chymotrypsin-like activity inhibitors, simultaneously, $R_1$ is isobutyl, $R_2$ is phenylmethyl, $R_3$ is isobutyl, and $R_4$ is 2-phenylethyl, and $R_5$ is acetyl. The peptide having such values is referred to herein as peptide (b).

In some embodiments of PGPH activity inhibitors, $R_1$ is hydrogen, $C_{1-6}$alkyl. In some embodiments of PGPH activity inhibitors, $R_1$ is isobutyl. In some embodiments of PGPH activity inhibitors, $R_2$ is hydrogen, $C_{1-6}$alkyl or aryl. In some embodiments of PGPH activity inhibitors, $R_2$ is phenyl, phenylmethyl, or 1-naphthyl. In some embodiments of PGPH activity inhibitors, $R_3$ is hydrogen or $C_{1-6}$carbocyclyl bonded to the $R_3$ backbone unit. In some embodiments of PGPH activity inhibitors, $R_3$ is ethylene bonded to the amine of the $R_3$ amino acid backbone, such as would be the case for the amino acid proline. In some optional embodiments of PGPH activity inhibitors, $R_4$ is hydrogen, $C_{1-6}$alkyl, aryl, and aryl-substituted $C_{1-6}$alkyl. In some other optional embodiments of PGPH activity inhibitors, $R_4$ is hydrogen, or isopropyl. In some optional embodiments of PGPH activity inhibitors, $R_5$ is hydrogen, $C_{1-6}$alkanoyl, aryl, heteroaryl, where substituents include halogen, carbonyl, monosubstituted-, disubstituted- or unsubstituted-amino, nitro, hydroxy, aryl, and $C_{1-5}$alkyl. In some optional embodiments of PGPH activity inhibitors, $R_5$ is acetyl, N-acetyl-piperidinecarbonyl, N-dimethylaminobenzyl, isooctanoic, or benzoylbenzoic.

In some preferred embodiments of PGPH activity inhibitors, simultaneously, $R_1$ is isobutyl, $R_2$ is phenyl, $R_3$ is ethylene bonded to the $R_3$ amine of the amino acid backbone, and $R_4$ is hydrogen, and $R_5$ is acetyl.

Group 2

In another embodiment, the proteasome inhibitor used in the invention includes at least four backbone units and has a structure of formula (III) or a pharmaceutically acceptable salt thereof,

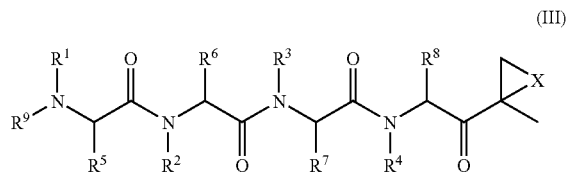

(III)

where X is O, NH, or N-alkyl, preferably O;

$R^1$, $R^2$, $R^3$, and $R^4$ are independently selected from hydrogen and a group of formula (IIIa), with the proviso that at least one of $R^1$, $R^2$, $R^3$, and $R^4$ is a group of formula (IIIa);

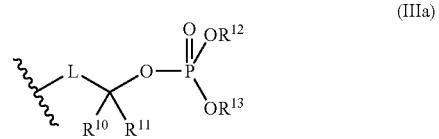

(IIIa)

$R^5$, $R^6$, $R^7$, and $R^8$ are independently selected from $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether;

$R^9$ is a further chain of amino acids, hydrogen, $C_{1-6}$acyl, a protecting group, aryl, or heteroaryl, where substituents include halogen, carbonyl, nitro, hydroxy, aryl, and $C_{1-5}$alkyl;

$R^{10}$ and $R^{11}$ are independently selected from hydrogen and $C_{1-6}$alkyl, or $R^{10}$ and $R^{11}$ together form a 3- to 6-membered carbocyclic or heterocyclic ring;

$R^{12}$ and $R^{13}$ are independently selected from hydrogen, a metal cation, $C_{1-6}$alkyl, and $C_{1-6}$aralkyl, or $R^{12}$ and $R^{13}$ together represent $C_{1-6}$alkyl, thereby forming a ring; and L is absent or is selected from —$CO_2$ or —C(=S)O.

Suitable N-terminal protecting groups known in the art of peptide synthesis, include t-butoxy carbonyl (Boc), benzoyl (Bz), fluoren-9-ylmethoxycarbonyl (Fmoc), triphenylmethyl (trityl) and trichloroethoxycarbonyl (Troc) and the like. The use of various N-protecting groups, e.g., the benzyloxy carbonyl group or the t-butyloxycarbonyl group (Boc), various coupling reagents, e.g., dicyclohexylcarbodiimide (DCC), 1,3-diisopropylcarbodiimide (DIC), 1-(3-dimethylaminopropyl)-3-ethylcarbodiimide (EDC), N-hydroxyazabenzotriazole (HATU), carbonyldiimidazole, or 1-hydroxybenzotriazole monohydrate (HOBT), and various cleavage conditions: for example, trifluoroacetic acid (TFA), HCl in dioxane, hydrogenation on Pd—C in organic solvents (such as methanol or ethyl acetate), boron tris(trifluoroacetate), and cyanogen bromide, and reaction in solution with isolation and purification of intermediates are well-known in the art of peptide synthesis, and are equally applicable to the preparation of the subject compounds.

In some embodiments, any two of $R^1$, $R^2$, $R^3$, and $R^4$ are hydrogen and any two of $R^1$, $R^2$, $R^3$, and $R^4$ have a structure of formula (IIIa). In preferred embodiments any three of $R^1$, $R^2$, $R^3$, and $R^4$ are hydrogen and any one of $R^1$, $R^2$, $R^3$, and $R^4$ has a structure of formula (IIIa). In the most preferred embodiment, $R^1$ has a structure of formula (IIIa) and $R^2$, $R^3$, and $R^4$ are hydrogen.

In certain embodiments, $R^5$, $R^6$, $R^7$, and $R^8$ are $C_{1-6}$alkyl or $C_{1-6}$aralkyl. In preferred embodiments, $R^6$ and $R^8$ are $C_{1-6}$alkyl and $R^5$ and $R^7$ are $C_{1-6}$aralkyl. In the most preferred embodiment, $R^6$ and $R^8$ are isobutyl, $R^5$ is 2-phenylethyl, and $R^7$ is phenylmethyl. In certain embodiments, $R^9$ is selected from hydrogen, $C_{1-6}$acyl, or a protecting group. In preferred embodiments, $R^9$ is hydrogen or acetyl. In the most preferred embodiment, $R^9$ is acetyl.

In certain embodiments, $R^{10}$ and $R^{11}$ are selected from hydrogen and $C_{1-6}$alkyl. In a preferred embodiment, $R^{10}$ is hydrogen and $R^{11}$ is $C_{1-6}$alkyl. In a further preferred embodiment, $R^{10}$ is hydrogen and $R^{11}$ is methyl. In another preferred embodiment, both $R^{10}$ and $R^{11}$ are hydrogen. In certain embodiments, $R^{12}$ and $R^{13}$ are $C_{1-6}$alkyl, metal cation, or $C_{1-6}$aralkyl. In certain preferred embodiments, $R^{12}$ and $R^{13}$ are selected from benzyl, tert-butyl, and sodium cation. In more preferred embodiments, both $R^{12}$ and $R^{13}$ are benzyl or tert-butyl. In the most preferred embodiment, at least one of $R^{12}$ and $R^{13}$ is a sodium cation.

In certain embodiments, a compound of formula (III) has the following stereochemistry:

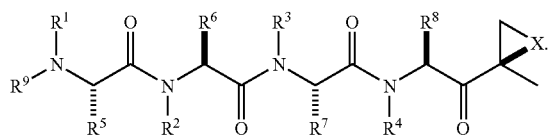

In preferred embodiments, the inhibitor has a structure of formula (IV) or a pharmaceutically acceptable salt thereof,

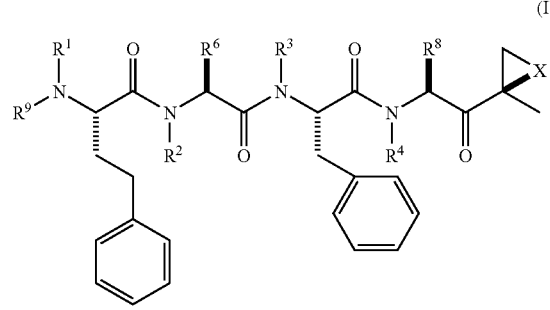

(IV)

where X is O, NH, or N-alkyl, preferably O;

$R^1$, $R^2$, $R^3$, and $R^4$ are independently selected from hydrogen and a group of formula (IIIa), with the proviso that at least one of $R^1$, $R^2$, $R^3$, and $R^4$ is a group of formula (IIIa);

$R^6$ and $R^8$ are independently selected from $C_{1-6}$alkyl, $C_{1-6}$hydroxy alkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether;

$R^9$ is a further chain of amino acids, hydrogen, acyl, a protecting group, aryl, or heteroaryl, where substituents include halogen, carbonyl, nitro, hydroxy, aryl, and $C_{1-5}$alkyl. Suitable N-terminal protecting groups known in the art of peptide synthesis, include t-butoxy carbonyl (Boc), benzoyl (Bz), fluoren-9-ylmethoxycarbonyl (Fmoc), triphenylmethyl (trityl) and trichloroethoxycarbonyl (Troc) and the like; and In some embodiments of chymotrypsin-like activity inhibitor prodrugs, any two of $R^1$, $R^2$, $R^3$, and $R^4$ are hydrogen and any two of $R^1$, $R^2$, $R^3$, and $R^4$ have a structure of formula (IIIa). In preferred embodiments any three of $R^1$, $R^2$, $R^3$, and $R^4$ are hydrogen and any one of $R^1$, $R^2$, $R^3$, and $R^4$ has a structure of formula (IIIa). In the most preferred embodiment, $R^1$ has a structure of formula (IIIa) and $R^2$, $R^3$, and $R^4$ are hydrogen.

In certain embodiments, $R^6$ and $R^8$ are $C_{1-6}$alkyl or $C_{1-6}$aralkyl. In preferred embodiments, $R^6$ and $R^8$ are $C_{1-6}$alkyl. In the most preferred embodiment, $R^6$ and $R^8$ are isobutyl. In certain embodiments, $R^9$ is selected from hydrogen, $C_{1-6}$acyl, or a protecting group. In preferred embodiments, $R^9$ is hydrogen or acetyl. In the most preferred embodiment, $R^9$ is acetyl.

In certain embodiments, $R^{10}$ and $R^{11}$ are selected from hydrogen and $C_{1-6}$alkyl. In a preferred embodiment, $R^{10}$ is hydrogen and $R^{11}$ is $C_{1-6}$alkyl. In a further preferred embodiment, $R^{10}$ is hydrogen and $R^{11}$ is methyl. In another preferred embodiment, both $R^{10}$ and $R^{11}$ are hydrogen. In certain embodiments, $R^{12}$ and $R^{13}$ are $C_{1-6}$alkyl, metal cation, or $C_{1-6}$aralkyl. In certain preferred embodiments, $R^{12}$ and $R^{13}$ are selected from benzyl, tert-butyl, and sodium cation. In more preferred embodiments, both $R^{12}$ and $R^{13}$ are benzyl or tert-butyl. In the most preferred embodiment, at least one of $R^{12}$ and $R^{13}$ is a sodium cation.

In some embodiments of PGPH activity inhibitors, any two of $R^1$, $R^2$, $R^3$, and $R^4$ are hydrogen and any two of $R^1$, $R^2$, $R^3$, and $R^4$ have a structure of formula (IIIa). In preferred embodiments any three of $R^1$, $R^2$, $R^3$, and $R^4$ are hydrogen and any one of $R^1$, $R^2$, $R^3$, and $R^4$ has a structure of formula (IIIa). In the most preferred embodiment, $R^1$ has a structure of formula (IIIa) and $R^2$, $R^3$, and $R^4$ are hydrogen.

In certain embodiments, $R^6$ and $R^8$ are $C_{1-6}$ alkyl. In preferred embodiments, $R^6$ and $R^8$ are isobutyl. In preferred embodiments, $R^9$ is hydrogen or acetyl. In the most preferred embodiments, $R^9$ is acetyl. In a preferred embodiment, $R^{10}$ is hydrogen and $R^{11}$ is methyl. In another preferred embodiment, both $R^{10}$ and $R^{11}$ are hydrogen. In certain embodiments, $R^{12}$ and $R^{13}$ are $C_{1-6}$alkyl, metal cation, or $C_{1-6}$aralkyl. In certain preferred embodiments, $R^{12}$ and $R^{13}$ are selected from benzyl, tert-butyl, and sodium cation. In more preferred embodiments, both $R^{12}$ and $R^{13}$ are benzyl or tert-butyl. In the most preferred embodiment, at least one of $R^{12}$ and $R^{13}$ is a sodium cation.

Group 3

In another embodiment, the proteasome inhibitor has a structure of formula (V) or is a pharmaceutically acceptable salt thereof:

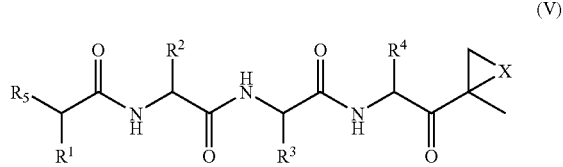

(V)

where:

each A is independently selected from C=O, C=S, and SO$_2$, preferably C=O;

L is absent or is selected from C=O, C=S, and SO$_2$, preferably L is absent or C=O;

M is absent or is C$_{1-6}$alkyl;

Q is absent or is selected from O, NH, and N—C$_{1-6}$alkyl, preferably Q is absent, O, or NH, most preferably Q is absent or O;

X is selected from O, NH, and N—C$_{1-6}$alkyl, preferably O;

Y is absent or is selected from O, NH, N—C$_{1-6}$alkyl, S, SO, SO$_2$, CHOR$^{10}$, and CHCO$_2$R$^{10}$;

each Z is independently selected from O, S, NH, and N—C$_{1-6}$alkyl, preferably O;

R$^1$, R$^2$, R$^3$, and R$^4$ are each independently selected from C$_{1-6}$alkyl, C$_{1-6}$hydroxyalkyl, C$_{1-6}$alkoxyalkyl, aryl, C$_{1-6}$aralkyl, heteroaryl, C$_{1-6}$heteroaralkyl, heterocyclyl, and C$_{1-6}$heterocycloalkyl, any of which is optionally substituted with one or more of amide, amine, carboxylic acid (or a salt thereof), ester (including C$_{1-5}$ alkyl ester and aryl ester), thiol, or thioether substituents;

R$^5$ is N(R$^6$)LQR$^7$;

R$^6$ is selected from hydrogen, OH, and C$_{1-6}$alkyl, preferably C$_{1-6}$alkyl;

R$^7$ is selected from hydrogen, C$_{1-6}$alkyl, C$_{1-6}$alkenyl, C$_{1-6}$alkynyl, aryl, C$_{1-6}$aralkyl, heteroaryl, C$_{1-6}$heteroaralkyl, R$^8$ZA-C$_{1-8}$alkyl-, R$^{11}$Z—C$_{1-8}$alkyl-, (R$^8$O)(R$^9$O)P(=O)O—C$_{1-8}$alkyl-ZAZ—C$_{1-8}$alkyl-, (R$^8$O)(R$^9$O)P(=O)O—C$_{1-8}$alkyl-Z—C$_{1-8}$alkyl-, R$^8$ZA-C$_{1-8}$alkyl-ZAZ—C$_{1-8}$alkyl-, heterocyclylMZAZ—C$_{1-8}$alkyl-, (R$^8$O)(R$^9$O)P(=O)O—C$_{1-8}$alkyl-, (R$^{10}$)$_2$N—C$_{1-8}$alkyl-, (R$^{10}$)$_3$N$^+$—C$_{1-8}$alkyl-, heterocyclylM-, carbocyclylM-, R$^{11}$SO$_2$C$_{1-8}$alkyl-, and R$^{11}$SO$_2$NH—; or R$^6$ and R$^7$ together are C$_{1-6}$alkyl-Y—C$_{1-6}$alkyl, C$_{1-6}$alkyl-ZA-C$_{1-6}$alkyl, A-C$_{1-6}$alkyl-ZA-C$_{1-6}$alkyl, A-C$_{1-6}$alkyl-A, or C$_{1-6}$alkyl-A, preferably C$_{1-2}$alkyl-Y—C$_{1-2}$alkyl, C$_{1-2}$alkyl-ZA-C$_{1-2}$alkyl, A-C$_{1-2}$alkyl-ZA-C$_{1-2}$alkyl, A-C$_{1-3}$alkyl-A, or C$_{1-4}$alkyl-A, thereby forming a ring;

R$^8$ and R$^9$ are independently selected from hydrogen, metal cation, C$_{1-6}$alkyl, C$_{1-6}$alkenyl, C$_{1-6}$alkynyl, aryl, heteroaryl, C$_{1-6}$aralkyl, and C$_{1-6}$heteroaralkyl, preferably from hydrogen, metal cation, and C$_{1-6}$alkyl, or R$^8$ and R$^9$ together are C$_{1-6}$alkyl, thereby forming a ring;

each R$^{10}$ is independently selected from hydrogen and C$_{1-6}$alkyl, preferably C$_{1-6}$alkyl; and R$^{11}$ is independently selected from hydrogen, C$_{1-6}$alkyl, C$_{1-6}$alkenyl, C$_{1-6}$alkynyl, carbocyclyl, heterocyclyl, aryl, heteroaryl, C$_{1-6}$aralkyl, and C$_{1-6}$heteroaralkyl, provided that when R$_6$ is H, L is C=O, and Q is absent, R$^7$ is not hydrogen, C$_{1-6}$alkyl, or aryl or heteroaryl.

In some embodiments, R$^1$, R$^2$, R$^3$, and R$^4$ are selected from C$_{1-6}$alkyl or C$_{1-6}$aralkyl. In preferred embodiments, R$^2$ and R$^4$ are C$_{1-6}$alkyl and R$^1$ and R$^3$ are C$_{1-6}$aralkyl. In the most preferred embodiment, R$^2$ and R$^4$ are isobutyl, R$^1$ is 2-phenylethyl, and R$^3$ is phenylmethyl.

In certain embodiments, L and Q are absent and R$^7$ is selected from C$_{1-6}$alkyl, C$_{1-6}$alkenyl, C$_{1-6}$alkynyl, C$_{1-6}$aralkyl, and C$_{1-6}$heteroaralkyl. In certain such embodiments, R$^6$ is C$_{1-6}$alkyl and R$^7$ is selected from butyl, allyl, propargyl, phenylmethyl, 2-pyridyl, 3-pyridyl, and 4-pyridyl.

In other embodiments, L is SO$_2$, Q is absent, and R$^7$ is selected from C$_{1-6}$alkyl and aryl. In certain such embodiments, R$^7$ is selected from methyl and phenyl.

In certain embodiments, L is C=O and R$^7$ is selected from C$_{1-6}$alkyl, C$_{1-6}$alkenyl, C$_{1-6}$alkynyl, aryl, C$_{1-6}$aralkyl, heteroaryl, C$_{1-6}$heteroaralkyl, R$^8$ZA-C$_{1-8}$alkyl-, R$^{11}$Z—C$_{1-8}$alkyl-, (R$^8$O)(R$^9$O)P(=O)O—C$_{1-8}$alkyl-, (R$^8$O)(R$^9$O)P(=O)O—C$_{1-8}$alkyl-ZAZ—C$_{1-8}$alkyl-, (R$^8$O)(R$^9$O)P(=O)O—C$_{1-8}$alkyl-Z—C$_{1-8}$alkyl-, R$^8$ZA-C$_{1-8}$alkyl-ZAZ—C$_{1-8}$alkyl-, heterocyclylMZAZ—C$_{1-8}$alkyl-, (R$^{10}$)$_2$N—C$_{1-8}$alkyl-, (R$^{10}$)$_3$N$^+$—C$_{1-8}$alkyl-, heterocyclylM-, carbocyclylM-, R$^{11}$SO$_2$C$_{1-8}$alkyl-, and R$^{11}$SO$_2$NH—. In certain embodiments, L is C=O, Q is absent, and R$^7$ is H.

In certain embodiments, R$^6$ is C$_{1-6}$alkyl, R$^7$ is C$_{1-6}$alkyl, Q is absent, and L is C=O. In certain such embodiments, R$^7$ is ethyl, isopropyl, 2,2,2-trifluoroethyl, or 2-(methylsulfonyl)ethyl.

In other embodiments, L is C=O, Q is absent, and R$^7$ is C$_{1-6}$aralkyl. In certain such embodiments, R$^7$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, R$^6$ is C$_{1-6}$alkyl, and R$^7$ is aryl. In certain such embodiments, R$^7$ is phenyl.

In certain embodiments, L is C=O, Q is absent or O, n is 0 or 1, and R$^7$ is —(CH$_2$)$_n$carbocyclyl. In certain such embodiments, R$^7$ is cyclopropyl or cyclohexyl.

In certain embodiments, L and A are C=O, Q is absent, Z is O, n is an integer from 1 to 8 (preferably 1), and R$^7$ is selected from R$^8$ZA-C$_{1-8}$alkyl-, R$^{11}$Z—C$_{1-8}$alkyl-, R$^8$ZA-C$_{1-8}$alkyl-ZAZ—C$_{1-8}$alkyl-, (R$^8$O)(R$^9$O)P(=O)O—C$_{1-8}$alkyl-ZAZ—C$_{1-8}$alkyl-, (R$^8$O)(R$^9$O)P(=O)—C$_{1-8}$alkyl-Z—C$_{1-8}$alkyl-, and heterocyclylMZAZ—C$_{1-8}$alkyl-. In certain such embodiments, R$^7$ is heterocyclylMZAZ—C$_{1-8}$alkyl- where heterocyclyl is oxodioxolenyl or N(R$^{12}$)(R$^{13}$), wherein R$^{12}$ and R$^{13}$ together are C$_{1-6}$alkyl-Y—C$_{1-6}$alkyl, preferably C$_{1-3}$alkyl-Y—C$_{1-3}$alkyl, thereby forming a ring.

In certain preferred embodiments, L is C=O, Q is absent, n is an integer from 1 to 8, and R$^7$ is selected from (R$^8$O)(R$^9$O)P(=O)O—C$_{1-8}$alkyl-, (R$^{10}$)$_2$NC$_{1-8}$alkyl, (R$^{10}$)$_3$N$^+$(CH$_2$)$_n$-, and heterocyclyl-M—. In certain such embodiments, R$^7$ is —C$_{1-8}$alkylN(R$^{10}$)$_2$ or —C$_{1-8}$alkylN$^+$(R$^{10}$)$_3$; where R$^{10}$ is C$_{1-6}$alkyl. In certain other such embodiments, R$^7$ is heterocyclylM-, where heterocyclyl is selected from morpholino, piperidino, piperazino, and pyrrolidino.

In certain embodiments, L is C=O, R$^6$ is C$_{1-6}$alkyl, Q is selected from O and NH and R$^7$ is selected from C$_{1-6}$alkyl, cycloalkyl-M, C$_{1-6}$aralkyl, and C$_{1-6}$heteroaralkyl. In other embodiments, L is C=O, R$^6$ is C$_{1-6}$alkyl, Q is selected from O and NH, and R$^7$ is C$_{1-6}$alkyl, where C$_{1-6}$alkyl is selected from methyl, ethyl, and isopropyl. In further embodiments, L is C=O, R$^6$ is C$_{1-6}$alkyl, Q is selected from O and NH and R$^7$ is C$_{1-6}$aralkyl, where aralkyl is phenylmethyl. In other embodiments, L is C=O, R$^6$ is C$_{1-6}$alkyl, Q is selected from O and NH, and R$^7$ is C$_{1-6}$heteroaralkyl, where heteroaralkyl is (4-pyridyl)methyl.

In certain embodiments, L is absent or is C=O, and R$^6$ and R$^7$ together are C$_{1-6}$alkyl-Y—C$_{1-6}$alkyl, C$_{1-6}$alkyl-ZA-C$_{1-6}$alkyl, or C$_{1-6}$alkyl-A, thereby forming a ring. In certain preferred embodiments, L is C=O, Q and Y are absent, and R$^6$ and R$^7$ together are C$_{1-3}$alkyl-Y—C$_{1-3}$alkyl. In another preferred embodiment, L and Q are absent, and R$^6$ and R$^7$ together are C$_{1-3}$alkyl-Y—C$_{1-3}$alkyl. In another preferred embodiment, L is C=O, Q is absent, Y is selected from NH and N—C$_{1-6}$alkyl, and R$^6$ and R$^7$ together are C$_{1-3}$alkyl-Y—C$_{1-3}$alkyl. In another preferred embodiment, L is C=O, Y is absent, and R$^6$ and R$^7$ together are C$_{1-3}$alkyl-Y—C$_{1-3}$alkyl. In another preferred embodiment, L and A are C=O, and R$^6$ and R$^7$ together are C$_{1-2}$alkyl-ZA-C$_{1-2}$alkyl. In another preferred embodiment, L and A are C=O and R$^6$ and R$^7$ together are C$_{2-3}$alkyl-A.

In certain embodiments, a compound of formula (V) has the following stereochemistry:

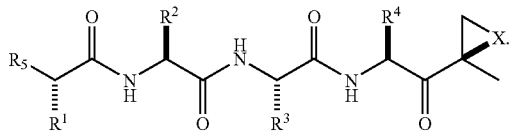

In preferred embodiments, the inhibitor has a structure of formula (VI) or a pharmaceutically acceptable salt thereof, (VI)

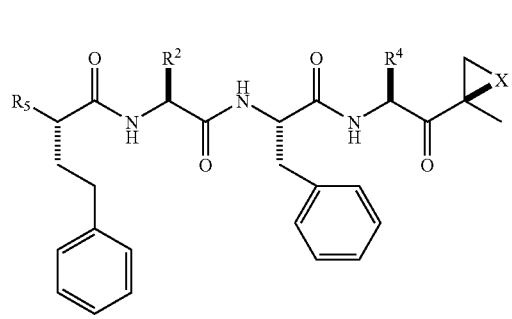

where:
each A is independently selected from C=O, C=S, and SO$_2$, preferably C=O;
L is absent or is selected from C=O, C=S, and SO$_2$, preferably L is absent or C=O;
M is absent or is C$_{1-8}$alkyl;
Q is absent or is selected from O, NH, and N—C$_{1-6}$alkyl, preferably Q is absent, O, or NH, most preferably Q is absent or O;
X is selected from O, NH, and N—C$_{1-6}$alkyl, preferably O;
Y is absent or is selected from O, NH, N—C$_{1-6}$alkyl, S, SO, SO$_2$, CHOR$^{10}$, and CHCO$_2$R$^{10}$;
each Z is independently selected from O, S, NH, and N—C$_{1-6}$alkyl, preferably O;
R$^2$ and R$^4$ are each independently selected from C$_{1-6}$alkyl, C$_{1-6}$hydroxyalkyl, C$_{1-6}$alkoxyalkyl, aryl, and C$_{1-6}$aralkyl, any of which is optionally substituted with one or more of amide, amine, carboxylic acid (or a salt thereof), ester (including C$_{1-5}$ alkyl ester and aryl ester), thiol, or thioether substituents;
R$^5$ is N(R$^6$)LQR$^7$;
R$^6$ is selected from hydrogen, OH, and C$_{1-6}$alkyl, preferably C$_{1-6}$alkyl;
R$^7$ is selected from hydrogen, C$_{1-6}$alkyl, C$_{1-6}$alkenyl, C$_{1-6}$alkynyl, aryl, C$_{1-6}$aralkyl, heteroaryl, C$_{1-6}$heteroaralkyl, R$^8$ZA-C$_{1-8}$alkyl-, R$^{11}$Z—C$_{1-8}$alkyl-, (R$^8$O)(R$^9$O)P(=O)O—C$_{1-8}$alkyl-ZAZ—C$_{1-8}$alkyl-, (R$^8$O)(R$^9$O)P(=O)O—C$_{1-8}$alkyl-Z—C$_{1-8}$alkyl-, R$^8$ZA-C$_{1-8}$alkyl-ZAZ—C$_{1-8}$alkyl-, heterocyclylMZAZ—C$_{1-8}$alkyl-, (R$^8$O)(R$^9$O)P(=O)O—C$_{1-8}$alkyl-, (R$^{10}$)$_2$N—C$_{1-8}$alkyl-, (R$^{10}$)$_3$N$^+$—C$_{1-8}$alkyl-, heterocyclylM-, carbocyclylM-, R$^{11}$SO$_2$C$_{1-8}$alkyl-, and R$^{11}$SO$_2$NH; or
R$^6$ and R$^7$ together are C$_{1-6}$alkyl-Y—C$_{1-6}$alkyl, C$_{1-6}$alkyl-ZA-C$_{1-6}$alkyl, A-C$_{1-6}$alkyl-ZA-C$_{1-6}$alkyl, A-C$_{1-6}$alkyl-A, or C$_{1-6}$alkyl-A, preferably C$_{1-2}$alkyl-Y—C$_{1-2}$alkyl, C$_{1-2}$alkyl-ZA-C$_{1-2}$alkyl, A-C$_{1-2}$alkyl-ZA-C$_{1-2}$alkyl, A-C$_{1-3}$alkyl-A, or C$_{1-4}$alkyl-A, thereby forming a ring;
R$^8$ and R$^9$ are independently selected from hydrogen, metal cation, C$_{1-6}$alkyl, C$_{1-6}$alkenyl, C$_{1-6}$alkynyl, aryl, heteroaryl, C$_{1-6}$aralkyl, and C$_{1-6}$heteroaralkyl, preferably from hydrogen, metal cation, and C$_{1-6}$alkyl, or R$^8$ and R$^9$ together are C$_{1-6}$alkyl, thereby forming a ring;
each R$^{10}$ is independently selected from hydrogen and C$_{1-6}$alkyl, preferably C$_{1-6}$alkyl;
R$^{11}$ is independently selected from hydrogen, C$_{1-6}$alkyl, C$_{1-6}$alkenyl, C$_{1-6}$alkynyl, carbocyclyl, heterocyclyl, aryl, heteroaryl, C$_{1-6}$aralkyl, and C$_{1-6}$heteroaralkyl; and
provided that when R$_6$ is H, L is C=O, and Q is absent, R$^7$ is not hydrogen, C$_{1-6}$alkyl, or aryl or heteroaryl.

In certain embodiments, L is C=O, Q is absent, X is O, R$^6$ is H, and R$^2$ and R$^4$ are selected from C$_{1-6}$alkyl and C$_{1-6}$aralkyl. In preferred such embodiments, R$^2$ and R$^4$ are C$_{1-6}$alkyl. In the most preferred such embodiment, R$^2$ and R$^4$ are isobutyl.

In certain embodiments, L is C=O, Q is absent, X is O, R$^6$ is H, R$^2$ and R$^4$ are isobutyl, and R$^7$ is heterocyclylM-, where the heterocycle is a nitrogen-containing heterocycle, such as piperazino (including N-(lower alkyl) piperazino), morpholino, and piperidino. In preferred such embodiments, M is CH$_2$. In the most preferred such embodiments, R$^7$ is morpholino.

In certain embodiments, a compound of formula (VI) has the following structure, also referred to as Compound A:

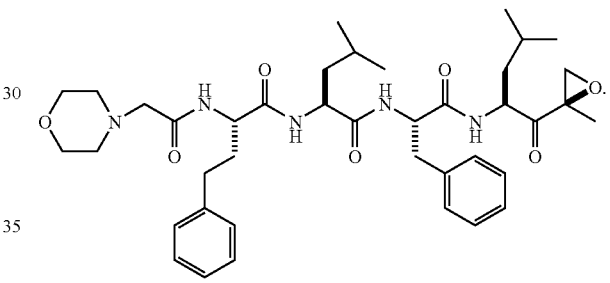

Group 4

In a further embodiment, the proteasome inhibitors have a structure of formula (VII) or a pharmaceutically acceptable salt thereof, (VII)

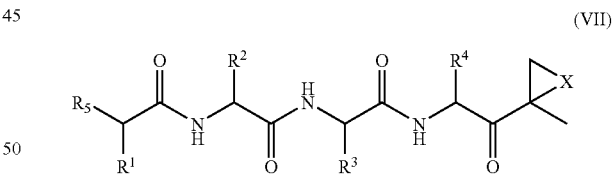

where:
each A is independently selected from C=O, C=S, and SO$_2$, preferably C=O;
each B is independently selected from C=O, C=S, and SO$_2$, preferably C=O;
D is absent or is C$_{1-8}$alkyl;
G is selected from O, NH, and N—C$_{1-6}$alkyl;
K is absent or is selected from C=O, C=S, and SO$_2$, preferably K is absent or is C=O;
L is absent or is selected from C=O, C=S, and SO$_2$, preferably L is absent or C=O;
M is absent or is C$_{1-8}$alkyl;
Q is absent or is selected from O, NH, and N—C$_{1-6}$alkyl, preferably Q is absent, O, or NH, most preferably Q is absent;

X is selected from O, S, NH, and N—$C_{1-6}$alkyl, preferably O;

each V is independently absent or is selected from O, S, NH, and N—$C_{1-6}$alkyl, preferably V is absent or O;

W is absent or is independently selected from O, S, NH, and N—$C_{1-6}$alkyl, preferably O;

Y is absent or is selected from O, NH, N—$C_{1-6}$alkyl, S, SO, $SO_2$, $CHOR^{10}$, and $CHCO_2R^{10}$;

each Z is independently selected from O, S, NH, and N—$C_{1-6}$alkyl, preferably O;

$R^1$, $R^2$, $R^3$, and $R^4$ are each independently selected from $C_{1-6}$alkyl, $C_{1-6}$hydroxyalkyl, $C_{1-6}$alkoxyalkyl, aryl, $C_{1-6}$aralkyl, heteroaryl, $C_{1-6}$heteroaralkyl, heterocyclyl, $C_{1-6}$heterocycloalkyl, and $R^{14}DVKOC_{1-3}$alkyl-, wherein at least one of $R^1$ and $R^3$ is $R^{14}DVKOC_{1-3}$alkyl-;

$R^5$ is $N(R^6)LQR^7$;

$R^6$ is selected from hydrogen, OH, and $C_{1-6}$alkyl, preferably $C_{1-6}$alkyl;

$R^7$ is a further chain of amino acids, hydrogen, a protecting group, aryl, or heteroaryl, any of which is optionally substituted with halogen, carbonyl, nitro, hydroxy, aryl, $C_{1-5}$alkyl; or $R^7$ is selected from $C_{1-6}$alkyl, $C_{1-6}$alkenyl, $C_{1-6}$alkynyl, $C_{1-6}$aralkyl, $C_{1-6}$heteroaralkyl, $R^8ZA$-$C_{1-8}$alkyl-, $R^{11}Z$—$C_{1-8}$alkyl-, $(R^8O)(R^9O)P(=O)O$—$C_{1-8}$alkyl-ZAZ—$C_{1-8}$alkyl-, $(R^8O)(R^9O)P(=O)O$—$C_{1-8}$alkyl-Z—$C_{1-8}$alkyl-, $R^8ZA$-$C_{1-8}$alkyl-ZAZ—$C_{1-8}$alkyl-, heterocyclylMZAZ—$C_{1-8}$alkyl-, $(R^8O)(R^9O)P(=O)O$—$C_{1-8}$alkyl-, $(R^{10})_2N$—$C_{1-8}$alkyl-, $(R^{10})_3N^+$—$C_{1-8}$alkyl-, heterocyclylM-, carbocyclylM-, $R^{11}SO_2C_{1-8}$alkyl-, and $R^{11}SO_2NH$; or $R^6$ and $R^7$ together are $C_{1-6}$alkyl-Y—$C_{1-6}$alkyl, $C_{1-6}$alkyl-ZA-$C_{1-6}$alkyl, A-$C_{1-6}$alkyl-ZA-$C_{1-6}$alkyl, A-$C_{1-6}$alkyl-A, or $C_{1-6}$alkyl-A, preferably $C_{1-2}$alkyl-Y—$C_{1-2}$alkyl, $C_{1-2}$alkyl-ZA-$C_{1-2}$alkyl, A-$C_{1-2}$alkyl-ZA-$C_{1-2}$alkyl, A-$C_{1-3}$alkyl-A, or $C_{1-4}$alkyl-A, thereby forming a ring, preferably $R^6$ is hydrogen and $R^7$ is $C_{1-6}$alkyl;

$R^8$ and $R^9$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^8$ and $R^9$ together are $C_{1-6}$alkyl, thereby forming a ring;

each $R^{10}$ is independently selected from hydrogen and $C_{1-6}$alkyl, preferably $C_{1-6}$alkyl;

$R^{11}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl, $R^{14}$ is selected from hydrogen, $(R^{15}O)(R^{16}O)P(=O)W$—, $R^{15}GB$—, heterocyclyl-, $(R^{17})_2N$—, $(R^{17})_3N^+$—, $R^{17}SO_2GBG$-, and $R^{15}GBC_{1-8}$alkyl- where the $C_{1-8}$alkyl moiety is optionally substituted with OH, $C_{1-8}$alkylW (optionally substituted with halogen, preferably fluorine), aryl, heteroaryl, carbocyclyl, heterocyclyl, and $C_{1-6}$aralkyl, preferably at least one occurrence of $R^{14}$ is other than hydrogen;

$R^{15}$ and $R^{16}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{15}$ and $R^{16}$ together are $C_{1-6}$alkyl, thereby forming a ring; and $R^{17}$ is selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

provided that when $R_6$ is H, L is C=O, and Q is absent, $R^7$ is not hydrogen, $C_{1-6}$alkyl, or aryl or heteroaryl; and D, G, V, K, and W are selected such that there are no O—O, N—O, S—N, or S—O bonds.

Suitable N-terminal protecting groups known in the art of peptide syntheses, include t-butoxy carbonyl (Boc), benzoyl (Bz), fluoren-9-ylmethoxycarbonyl (Fmoc), triphenylmethyl (trityl) and trichloroethoxycarbonyl (Troc) and the like. The use of various N-protecting groups, e.g., the benzyloxy carbonyl group or the t-butyloxycarbonyl group (Boc), various coupling reagents, e.g., dicyclohexylcarbodiimide (DCC), 1,3-diisopropylcarbodiimide (DIC), 1-(3-dimethylaminopropyl)-3-ethylcarbodiimide (EDC), N-hydroxyazabenzotriazole (HATU), carbonyldiimidazole, or 1-hydroxybenzotriazole monohydrate (HOBT), and various cleavage conditions: for example, trifluoroacetic acid (TFA), HCl in dioxane, hydrogenation on Pd—C in organic solvents (such as methanol or ethyl acetate), boron tris(trifluoroacetate), and cyanogen bromide, and reaction in solution with isolation and purification of intermediates are well-known in the art of peptide synthesis, and are equally applicable to the preparation of the subject compounds.

In certain embodiments, $R^1$, $R^2$, $R^3$, and $R^4$ are each independently selected from $C_{1-6}$alkyl, $C_{1-6}$hydroxyalkyl, $C_{1-6}$alkoxyalkyl, aryl, $C_{1-6}$aralkyl, and $R^{14}DVKOC_{1-3}$alkyl- wherein at least one of $R^1$ and $R^3$ is $R^{14}DVKOC_{1-3}$alkyl-. In preferred embodiments, one of $R^1$ and $R^3$ is $C_{1-6}$aralkyl and the other is $R^{14}DVKOC_{1-3}$alkyl-, and $R^2$ and $R^4$ are independently $C_{1-6}$alkyl. In the most preferred embodiment, one of $R^1$ and $R^3$ is 2-phenylethyl or phenylmethyl and the other is $R^{14}DVKOCH_2$— or $R^{14}DVKO(CH_3)CH$—, and both $R^2$ and $R^4$ are isobutyl.

In certain embodiments, L and Q are absent and $R^7$ is selected from hydrogen, a further chain of amino acids, $C_{1-6}$acyl, a protecting group, aryl, heteroaryl, $C_{1-6}$alkyl, $C_{1-6}$alkenyl, $C_{1-6}$alkynyl, $C_{1-6}$aralkyl, and $C_{1-6}$heteroaralkyl. In certain such embodiments, $R^6$ is $C_{1-6}$alkyl and $R^7$ is selected from butyl, allyl, propargyl, phenylmethyl, 2-pyridyl, 3-pyridyl, and 4-pyridyl.

In other embodiments, L is $SO_2$, Q is absent, and $R^7$ is selected from $C_{1-6}$alkyl and aryl. In certain such embodiments, $R^7$ is selected from methyl and phenyl.

In certain embodiments, L is C=O and $R^7$ is selected from $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^8ZA$-$C_{1-8}$alkyl-, $R^{11}Z$—$C_{1-8}$alkyl-, $(R^8O)(R^9O)P(=O)O$—$C_{1-8}$alkyl-, $(R^8O)(R^9O)P(=O)O$—$C_{1-8}$alkyl-ZAZ—$C_{1-8}$alkyl-, $(R^8O)(R^9O)P(=O)O$—$C_{1-8}$alkyl-Z—$C_{1-8}$alkyl-, $R^8ZA$-$C_{1-8}$alkyl-ZAZ—$C_{1-8}$alkyl-, heterocyclylMZAZ—$C_{1-8}$alkyl-, $(R^{10})_2N$—$C_{1-8}$alkyl-, $(R^{10})_3N^+$—$C_{1-8}$alkyl-, heterocyclylM-, carbocyclylM-, $R^{11}SO_2C_{1-8}$alkyl-, and $R^{11}SO_2NH$—. In certain embodiments, L is C=O, Q is absent, and $R^7$ is H.

In certain embodiments, $R^6$ is $C_{1-6}$alkyl, $R^7$ is $C_{1-6}$alkyl, Q is absent, and L is C=O. In certain such embodiments, $R^7$ is ethyl, isopropyl, 2,2,2-trifluoroethyl, or 2-(methylsulfonyl) ethyl.

In other embodiments, L is C=O, Q is absent, and $R^7$ is $C_{1-6}$aralkyl. In certain such embodiments, $R^7$ is selected from 2-phenylethyl, phenylmethyl, (4-methoxyphenyl)methyl, (4-chlorophenyl)methyl, and (4-fluorophenyl)methyl.

In other embodiments, L is C=O, Q is absent, $R^6$ is $C_{1-6}$alkyl, and $R^7$ is aryl. In certain such embodiments, $R^7$ is phenyl.

In certain embodiments, L is C=O, Q is absent or O, and $R^7$ is —$(CH_2)_n$carbocyclyl. In certain such embodiments, $R^7$ is cyclopropyl or cyclohexyl.

In certain embodiments, L and A are C=O, Q is absent, Z is O, and $R^7$ is selected from $R^8ZA$-$C_{1-8}$alkyl-, $R^{11}Z$—$C_{1-8}$alkyl-, $R^8ZA$-$C_{1-8}$alkyl-ZAZ—$C_{1-8}$alkyl-, $(R^8O)(R^9O)P(=O)O$—$C_{1-8}$alkyl-ZAZ—$C_{1-8}$alkyl-, $(R^8O)(R^9O)P(=O)O$—$C_{1-8}$alkyl-Z—$C_{1-8}$alkyl-, and heterocyclylMZAZ—$C_{1-8}$alkyl-. In certain such embodiments, $R^7$ is heterocyclylMZAZ—$C_{1-8}$alkyl- where heterocyclyl is oxodioxolenyl or N(R$^{12}$)(R$^{13}$), wherein R$^{12}$ and R$^{13}$ together are C$_{1-6}$alkyl-Y—C$_{1-6}$alkyl, preferably C$_{1-3}$alkyl-Y—C$_{1-3}$alkyl, thereby forming a ring.

In certain preferred embodiments, L is C=O, Q is absent, and R$^7$ is selected from (R$^8$O)(R$^9$O)P(=O)O—C$_{1-8}$alkyl-, (R$^{10}$)$_2$NC$_{1-8}$alkyl, (R$^{10}$)$_3$N$^+$(CH$_2$)$_n$—, and heterocyclyl-M—. In certain such embodiments, R$^7$ is —C$_{1-8}$alkylN(R$^{10}$)$_2$ or —C$_{1-8}$alkylN$^+$(R$^{10}$)$_3$, where R$^{10}$ is C$_{1-6}$alkyl. In certain other such embodiments, R$^7$ is heterocyclylM-, where heterocyclyl is selected from morpholino, piperidino, piperazino, and pyrrolidino.

In certain embodiments, L is C=O, R$^6$ is C$_{1-6}$alkyl, Q is selected from O and NH and R$^7$ is selected from C$_{1-6}$alkyl, cycloalkyl-M, C$_{1-6}$aralkyl, and C$_{1-6}$heteroaralkyl. In other embodiments, L is C=O, R$^6$ is C$_{1-6}$alkyl, Q is selected from O and NH, and R$^7$ is C$_{1-6}$alkyl, where C$_{1-6}$alkyl is selected from methyl, ethyl, and isopropyl. In further embodiments, L is C=O, R$^6$ is C$_{1-6}$alkyl, Q is selected from O and NH and R$^7$ is C$_{1-6}$aralkyl, where aralkyl is phenylmethyl. In other embodiments, L is C=O, R$^6$ is C$_{1-6}$alkyl, Q is selected from O and NH, and R$^7$ is C$_{1-6}$heteroaralkyl, where heteroaralkyl is (4-pyridyl)methyl.

In certain embodiments, L is absent or is C=O, and R$^6$ and R$^7$ together are C$_{1-6}$alkyl-Y—C$_{1-6}$alkyl, C$_{1-6}$alkyl-ZA-C$_{1-6}$alkyl, or C$_{1-6}$alkyl-A, thereby forming a ring. In certain preferred embodiments, L is C=O, Q and Y are absent, and R$^6$ and R$^7$ together are C$_{1-3}$alkyl-Y—C$_{1-3}$alkyl. In another preferred embodiment, L and Q are absent, and R$^6$ and R$^7$ together are C$_{1-3}$alkyl-Y—C$_{1-3}$alkyl. In another preferred embodiment, L is C=O, Q is absent, Y is selected from NH and N—C$_{1-6}$alkyl, and R$^6$ and R$^7$ together are C$_{1-3}$alkyl-Y—C$_{1-3}$alkyl. In another preferred embodiment, L is C=O, Y is absent, and R$^6$ and R$^7$ together are C$_{1-3}$alkyl-Y—C$_{1-3}$alkyl. In another preferred embodiment, L and A are C=O, and R$^6$ and R$^7$ together are C$_{1-2}$alkyl-ZA-C$_{1-2}$alkyl. In another preferred embodiment, L and A are C=O and R$^6$ and R$^7$ together are C$_{2-3}$alkyl-A.

In certain embodiments, R$^{14}$ is (R$^{15}$O)(R$^{16}$O)P(=O)W—. In certain such embodiments, D, V, K, and W are absent. In other such embodiments, V and K are absent, D is C$_{1-8}$alkyl, and W is O. In yet other such embodiments, D is C$_{1-8}$alkyl, K is C=O, and V and W are O.

In certain embodiments, R$^{14}$ is R$^{15}$GB—. In preferred embodiments, B is C=O, G is O, D is C$_{1-8}$alkyl, V is O, and K is C=O.

In certain embodiments, R$^{14}$ is heterocyclyl-. In preferred such embodiments, D is C$_{1-8}$alkyl. In certain such embodiments, V is O, K is C=O, and heterocyclyl is oxodioxolenyl. In other embodiments, V is absent, K is absent or is C=O, and heterocyclyl is N(R$^{18}$)(R$^{19}$), where R$^{18}$ and R$^{19}$ together are J-T-J, J-WB-J, or B-J-T-J, T is absent or is selected from O, NR$^{17}$, S, SO, SO$_2$, CHOR$^{17}$, CHCO$_2$R$^{15}$, C=O, CF$_2$, and CHF, and J is absent or is C$_{1-3}$alkyl.

In certain embodiments, R$^{14}$ is (R$^{17}$)$_2$N— or (R$^{17}$)$_3$N$^+$-, and preferably V is absent. In preferred such embodiments, D is C$_{1-8}$alkyl and K is absent or C=O. In certain embodiments where V is absent and R$^{14}$ is (R$^{17}$)$_2$N—, D is absent K is absent or is C=O, preferably K is C=O.

In certain embodiments, R$^{14}$ is R$^{17}$SO$_2$GBG-. In preferred such embodiments, B is C=O, D, V, and K are absent, and G is NH or NC$_{1-6}$alkyl.

In certain embodiments, R$^{14}$ is R$^{15}$GBC$_{1-8}$alkyl-. In preferred embodiments, B is C=O, G is O, and the C$_{1-8}$alkyl moiety is optionally substituted with OH, C$_{1-8}$alkyl (optionally substituted with halogen, preferably fluorine), C$_{1-8}$alkylW, aryl, heteroaryl, carbocyclyl, heterocyclyl, and C$_{1-6}$aralkyl. In certain such embodiments, the C$_{1-8}$alkyl moiety is an unsubstituted, mono-, or disubstituted C$_1$alkyl.

In certain embodiments, a compound of formula (VII) has the following stereochemistry:

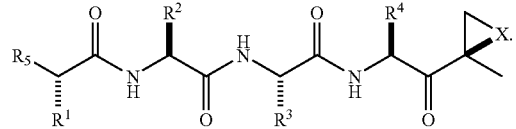

In preferred embodiments, the inhibitor has a structure of formula (VIII) or a pharmaceutically acceptable salt thereof, (VIII)

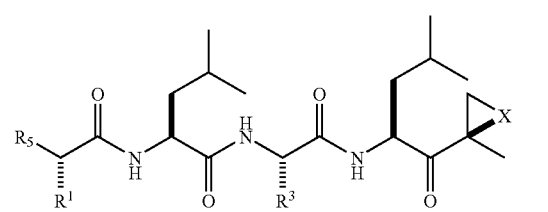

where:
each A is independently selected from C=O, C=S, and SO$_2$, preferably C=O;
each B is independently selected from C=O, C=S, and SO$_2$, preferably C=O;
D is absent or is C$_{1-8}$alkyl;
G is selected from O, NH, and N—C$_{1-6}$alkyl;
K is absent or is selected from C=O, C=S, and SO$_2$, preferably K is absent or is C=O;
L is absent or is selected from C=O, C=S, and SO$_2$, preferably L is absent or C=O;
M is absent or is C$_{1-8}$alkyl;
Q is absent or is selected from O, NH, and N—C$_{1-6}$alkyl, preferably Q is absent, O, or NH, most preferably Q is absent or O;
X is selected from O, S, NH, and N—C$_{1-6}$alkyl, preferably O;
each V is independently absent or is selected from O, S, NH, and N—C$_{1-6}$alkyl, preferably V is absent or O;
W is absent or is independently selected from O, S, NH, and N—C$_{1-6}$alkyl, preferably O;
Y is absent or is selected from O, NH, N—C$_{1-6}$alkyl, S, SO, SO$_2$, CHOR$^{10}$, and CHCO$_2$R$^{10}$;
each Z is independently selected from O, S, NH, and N—C$_{1-6}$alkyl, preferably O;
R$^1$ and R$^3$ are each independently selected from C$_{1-6}$alkyl, C$_{1-6}$hydroxyalkyl, C$_{1-6}$alkoxyalkyl, aryl, C$_{1-6}$aralkyl, and R$^{14}$DVKOC$_{1-3}$alkyl-, wherein at least one of R$^1$ and R$^3$ is R$^{14}$DVKOC$_{1-3}$alkyl-;
R$^5$ is N(R$^6$)LQR$^7$;
R$^6$ is selected from hydrogen, OH, and C$_{1-6}$alkyl, preferably C$_{1-6}$alkyl;
R$^7$ is a further chain of amino acids, hydrogen, a protecting group, aryl, or heteroaryl, any of which is optionally substituted with halogen, carbonyl, nitro, hydroxy, aryl, C$_{1-5}$alkyl; or R$^7$ is selected from C$_{1-6}$alkyl, C$_{1-6}$alkenyl, C$_{1-6}$alkynyl, C$_{1-6}$aralkyl, C$_{1-6}$heteroaralkyl, R$^8$ZA-C$_{1-8}$alkyl-, R$^{11}$Z—C$_{1-8}$alkyl-, (R$^8$O)(R$^9$O)P(=O)O—C$_{1-8}$alkyl-ZAZ—C$_{1-8}$alkyl-, (R$^8$O)(R$^9$O)P(=O)O—C$_{1-8}$alkyl-Z—C$_{1-8}$alkyl-, R$^8$ZA-C$_{1-8}$alkyl-ZAZ—C$_{1-8}$alkyl-, heterocyclylMZAZ—

$C_{1-8}$alkyl-, $(R^8O)(R^9O)P(=O)O-C_{1-8}$alkyl-, $(R^{10})_2N-C_{1-8}$alkyl-, $(R^{10})_3N^+-C_{1-8}$alkyl-, heterocyclylM-, carbocyclylM-, $R^{11}SO_2C_{1-8}$alkyl-, and $R^{11}SO_2NH$; or $R^6$ and $R^7$ together are $C_{1-6}$alkyl-Y-$C_{1-6}$alkyl, $C_{1-6}$alkyl-ZA-$C_{1-6}$alkyl, A-$C_{1-6}$alkyl-ZA-$C_{1-6}$alkyl, A-$C_{1-6}$alkyl-A, or $C_{1-6}$alkyl-A, preferably $C_{1-2}$alkyl-Y-$C_{1-2}$alkyl, $C_{1-2}$alkyl-ZA-$C_{1-2}$alkyl, A-$C_{1-2}$alkyl-ZA-$C_{1-2}$alkyl, A-$C_{1-3}$alkyl-A, or $C_{1-4}$alkyl-A, thereby forming a ring;

$R^8$ and $R^9$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^8$ and $R^9$ together are $C_{1-6}$alkyl, thereby forming a ring;

each $R^{10}$ is independently selected from hydrogen and $C_{1-6}$alkyl, preferably $C_{1-6}$alkyl; and $R^{11}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl, $R^{14}$ is selected from hydrogen, $(R^{15}O)(R^{16}O)P(=O)W-$, $R^{15}GB-$, heterocyclyl-, $(R^{17})_2N-$, $(R^{17})_3N^+-$, $R^{17}SO_2GBG-$, and $R^{15}GBC_{1-8}$alkyl- where the $C_{1-8}$alkyl moiety is optionally substituted with OH, $C_{1-8}$alkylW (optionally substituted with halogen, preferably fluorine), aryl, heteroaryl, carbocyclyl, heterocyclyl, and $C_{1-6}$aralkyl, preferably at least one occurrence of $R^{14}$ is other than hydrogen;

$R^{15}$ and $R^{16}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, preferably from hydrogen, metal cation, and $C_{1-6}$alkyl, or $R^{15}$ and $R^{16}$ together are $C_{1-6}$alkyl, thereby forming a ring;

$R^{17}$ is selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

provided that when $R_6$ is H, L is C=O, and Q is absent, $R^7$ is not hydrogen, $C_{1-6}$alkyl, or aryl or heteroaryl; and D, G, V, K, and W are selected such that there are no O—O, N—O, S—N, or S—O bonds.

Group 5

In one embodiment, the proteasome inhibitors have a structure of formula (IX) or a pharmaceutically acceptable salt thereof,

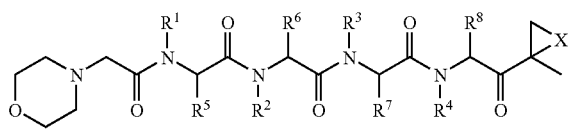

(IX)

where:

X is O, NH, or N-alkyl, preferably O;

$R^1, R^2, R^3$, and $R^4$ are independently selected from hydrogen and a group of formula (IXa), preferably, $R^1, R^2, R^3$, and $R^4$ are all the same, more preferably $R^1, R^2, R^3$, and $R^4$ are all hydrogen;

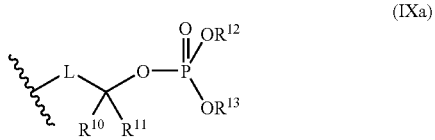

(IXa)

$R^5, R^6, R^7$, and $R^8$ are independently selected from H, $C_{1-6}$alkyl, $C_{1-6}$hydroxyalkyl, $C_{1-6}$alkoxyalkyl, aryl, $C_{1-6}$aralkyl, heteroaryl, $C_{1-6}$heteroaralkyl, heterocyclyl, and $C_{1-6}$heterocycloalkyl, each of which is optionally substituted with a group selected from amide, amine, carboxylic acid or a pharmaceutically acceptable salt thereof, carboxyl ester, thiol, and thioether, preferably $R^5, R^6, R^7$, and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl and $R^5$ and $R^7$ are independently $C_{1-6}$aralkyl;

$R^{10}$ and $R^{11}$ are independently selected from hydrogen and $C_{1-6}$alkyl, or $R^{10}$ and $R^{11}$ together form a 3- to 6-membered carbocyclic or heterocyclic ring;

$R^{12}$ and $R^{13}$ are independently selected from hydrogen, a metal cation, $C_{1-6}$alkyl, and $C_{1-6}$aralkyl, or $R^{12}$ and $R^{13}$ together represent $C_{1-6}$alkyl, thereby forming a ring.

In certain embodiments, X is O and $R^1, R^2, R^3$, and $R^4$ are all the same, preferably $R^1, R^2, R^3$, and $R^4$ are all hydrogen. In certain such embodiments, $R^5, R^6, R^7$, and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl and $R^5$ and $R^7$ are independently $C_{1-6}$aralkyl.

In certain preferred embodiments, X is O, $R^1, R^2, R^3$, and $R^4$ are all hydrogen, $R^6$ and $R^8$ are both isobutyl, $R^5$ is phenylethyl, and $R^7$ is phenylmethyl.

In certain embodiments, a compound of formula (IX) has the following stereochemistry:

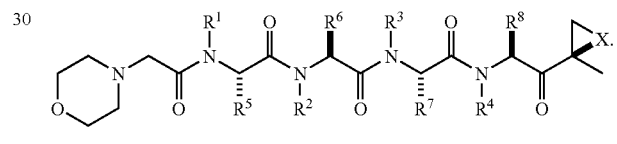

In preferred embodiments, the inhibitor has a structure of formula (X) or a pharmaceutically acceptable salt thereof,

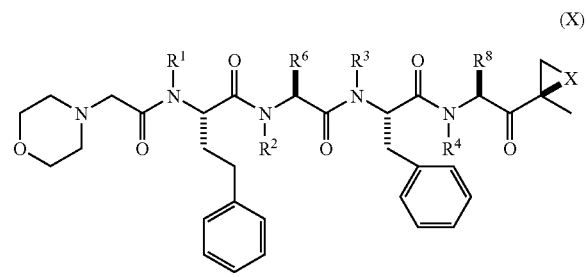

(X)

where:

X is O, NH, or N-alkyl, preferably O;

$R^1, R^2, R^3$, and $R^4$ are independently selected from hydrogen and a group of formula (IXa), preferably, $R^1, R^2, R^3$, and $R^4$ are all the same, more preferably $R^1, R^2, R^3$, and $R^4$ are all hydrogen;

$R^6$ and $R^8$ are independently selected from H, $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether, preferably $R^6$ and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl.

In certain embodiments, X is O and $R^1, R^2, R^3$, and $R^4$ are all the same, preferably $R^1, R^2, R^3$, and $R^4$ are all hydrogen. In certain such embodiments, $R^6$ and $R^8$ are independently selected from $C_{1-6}$alkyl, $C_{1-6}$hydroxyalkyl, and $C_{1-6}$aralkyl, more preferably, $R^6$ and $R^8$ are independently $C_{1-6}$alkyl.

In certain preferred embodiments, X is O, $R^1$, $R^2$, $R^3$, and $R^4$ are all hydrogen, and $R^6$ and $R^8$ are both isobutyl.

In certain embodiments, a compound of formula (X) has the following structure:

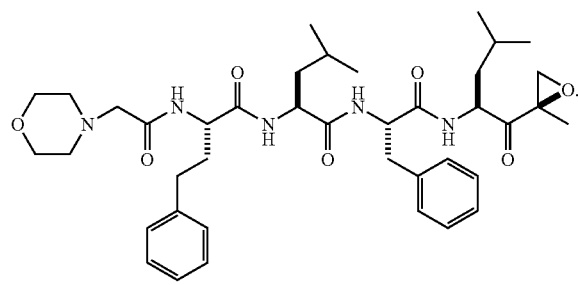

Group 6

In certain embodiments, the proteasome inhibitors have a structure of formula (XI) or a pharmaceutically acceptable salt thereof,

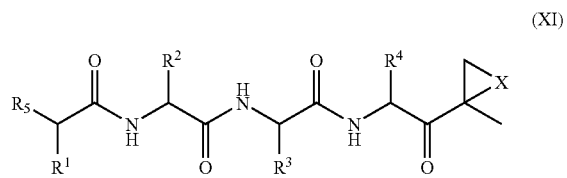

where:

X is selected from O, NH, and N—$C_{1-6}$alkyl, preferably O;

$R^1$, $R^2$, $R^3$, and $R^4$ are each independently selected from $C_{1-6}$alkyl, $C_{1-6}$hydroxyalkyl, $C_{1-6}$alkoxyalkyl, aryl, $C_{1-6}$aralkyl, heteroaryl, $C_{1-6}$heteroaralkyl, heterocyclyl, and $C_{1-6}$heterocycloalkyl, any of which is optionally substituted with one or more of amide, amine, carboxylic acid (or a salt thereof), ester (including $C_{1-5}$alkyl ester and aryl ester), thiol, or thioether substituents;

$R^5$ is $N(R^6)R^7$;

$R^6$ is selected from hydrogen, OH, and $C_{1-6}$alkyl, preferably H or $C_{1-6}$alkyl; and $R^7$ is a detectable label, such as a fluorescent moiety, a chemiluminescent moiety, a paramagnetic contrast agent, a metal chelate, a radioactive isotope-containing moiety (e.g., a moiety containing one or more tritium atoms), biotin, or a moiety that selectively binds to an antibody.

In some embodiments, $R^1$, $R^2$, $R^3$, and $R^4$ are selected from $C_{1-6}$alkyl or $C_{1-6}$aralkyl. In preferred embodiments, $R^2$ and $R^4$ are $C_{1-6}$alkyl and $R^1$ and $R^3$ are $C_{1-6}$aralkyl. In the most preferred embodiment, $R^2$ and $R^4$ are isobutyl, $R^1$ is 2-phenylethyl, and $R^3$ is phenylmethyl.

In certain embodiments, $R^6$ is selected from H or $C_{1-6}$alkyl. In certain preferred embodiments, $R^6$ is H.

In certain embodiments, $R^7$ is a covalently conjugated moiety selected from a fluorescent moiety, a radioactive isotope-containing moiety, biotin, and a moiety that selectively binds to an antibody.

In certain embodiments, $R^7$ is a fluorescent moiety. In certain such embodiments, the fluorescent moiety is an amine-reactive dye that has been covalently attached to the inhibitor. In preferred such embodiments, the amine-reactive dye is selected from Alexa Fluor dyes, BODIPY dyes, Cascade Blue dyes, coumarin, digoxigenin, fluorescein, lissamine rhodamine B dyes, Oregon Green dyes, rhodamine 6G dyes, rhodamine green dyes, rhodamine red dyes, Tamra, tetramethylrhodamine, and Texas Red dyes. In certain preferred embodiments, $R^7$ is a fluorescent moiety selected from fluorescein, tetramethylrhodamine, and Tamra.

There are generally four classes of commonly used dye reagents to label amines: succinimidyl esters, isothiocyanates, sulfonyl chlorides, and tetrafluorophenyl esters. Generally succinimidyl esters and tetrafluorophenyl esters are preferred for conjugation to proteins and peptides since they form a stable amide bond between the dye and the protein. Useful reviews that provide information on the conjugation of an amine-reactive dye to a protein or peptide sequence can be found in Bioconjug. Chem. 3, 2 (1992) and Methods Mol. Biol. 45, 205 (1995), incorporated herein by reference in their entirety. Information on the purchase and use of amine-reactive dyes is also available from Molecular Probes, Inc.

In certain embodiments, $R^7$ contains a radioactive moiety. In certain such embodiments, $R^7$ is selected from $C_{1-6}$alkyl, $C_{1-6}$hydroxyalkyl, $C_{1-6}$alkoxyalkyl, aryl, and $C_{1-6}$aralkyl, wherein $R^7$ includes at least one radioactive label selected from $^3H$, $^{11}C$, $^{14}C$, $^{13}N$, $^{15}O$, and $^{125}I$. In preferred such embodiments, $R^7$ is an amino acid or peptide moiety that includes at least one radioactive label selected from $^{11}C$, $^{14}C$, $^{13}N$, $^{15}O$, and $^{125}I$.

In certain embodiments, $R^7$ comprises a covalently conjugated moiety that selectively binds to an antibody that specifically binds to a peptide. In preferred embodiments, the moiety is selected from FLAG™, HA, HIS, c-Myc, VSV-G, V5 and HSV.

Preparation of inhibitors where $R^7$ comprises a moiety selected from FLAG™, HA, HIS, c-Myc, VSV-G, V5 and HSV may be accomplished using standard peptide coupling chemistry.

In certain embodiments, $R^7$ is biotin which may be covalently conjugated to the inhibitor using standard carboxylic acid/amine coupling chemistry.

In certain embodiments, a compound of formula (XI) has the following stereochemistry:

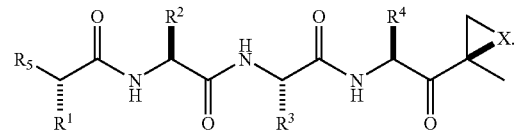

In preferred embodiments, the inhibitor has a structure of formula (XII) or a pharmaceutically acceptable salt thereof,

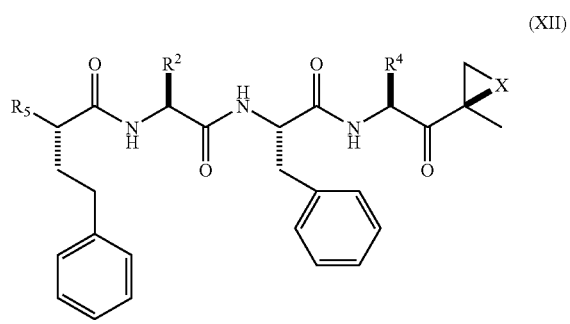

where:

X is selected from O, NH, and N—$C_{1-6}$alkyl, preferably O;

$R^2$ and $R^4$ are each independently selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid (or a salt thereof), ester (including $C_{1-5}$alkyl ester and aryl ester), thiol, or thioether substituents;

$R^5$ is $N(R^6)R^7$;

$R^6$ is selected from hydrogen, OH, and $C_{1-6}$alkyl, preferably $C_{1-6}$alkyl;

$R^7$ comprises a detectable label, such as a fluorescent moiety, a chemiluminescent moiety, a paramagnetic contrast agent, a metal chelate, a radioactive isotope-containing moiety, biotin, or a moiety that selectively binds to an antibody.

Group 7

In certain embodiments, the proteasome inhibitors have a structure of formula (XIII) or formula (XIV) or a pharmaceutically acceptable salt thereof,

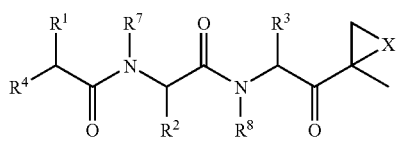

(XIII)

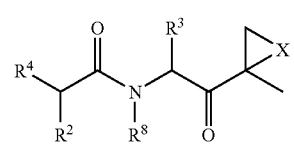

(XIV)

where:

each Ar is independently an aromatic or heteroaromatic group optionally substituted with 1 to 4 substituents;

L is selected from C=O, C=S, and $SO_2$, preferably $SO_2$ or C=O;

X is selected from O, S, NH, and N—$C_{1-6}$alkyl, preferably O;

Y is absent or is selected from C=O and $SO_2$;

Z is absent or is $C_{1-6}$alkyl;

$R^1$, $R^2$, and $R^3$ are each independently selected from $C_{1-6}$alkyl, $C_{1-6}$hydroxyalkyl, $C_{1-6}$alkoxyalkyl, aryl, $C_{1-6}$aralkyl, heteroaryl, $C_{1-6}$heteroaralkyl, heterocyclyl, and $C_{1-6}$heterocycloalkyl, any of which is optionally substituted with one or more of amide, amine, carboxylic acid (or a salt thereof), ester (including $C_{1-5}$ alkyl ester and aryl ester), thiol, or thioether substituents;

$R^4$ is $N(R^5)L$-Z—$R^6$;

$R^5$ is selected from hydrogen, OH, $C_{1-6}$aralkyl, and $C_{1-6}$alkyl, preferably hydrogen;

$R^6$ is selected from hydrogen, $C_{1-6}$alkenyl, Ar—Y—, carbocyclyl, and heterocyclyl; and $R^7$ and $R^8$ are independently selected from hydrogen, $C_{1-6}$alkyl, and $C_{1-6}$aralkyl, preferably hydrogen.

In certain embodiments, X is O and $R^1$, $R^2$, and $R^3$ are each independently selected from $C_{1-6}$alkyl, $C_{1-6}$hydroxyalkyl, and $C_{1-6}$aralkyl. In preferred such embodiments, $R^1$ and $R^3$ are independently $C_{1-6}$alkyl and $R^2$ is $C_{1-6}$aralkyl. In more preferred such embodiments, $R^1$ and $R^3$ are both isobutyl and $R^2$ is phenylmethyl.

In certain embodiments, $R^5$ is hydrogen, L is C=O or $SO_2$, $R^6$ is Ar—Y—, and each Ar is independently selected from phenyl, indolyl, benzofuranyl, naphthyl, quinolinyl, quinolo- nyl, thienyl, pyridyl, pyrazyl, and the like. In certain such embodiments, Ar may be substituted with Ar—Q—, where Q is selected from a direct bond, —O—, and $C_{1-6}$alkyl. In certain other such embodiments where Z is $C_{1-6}$alkyl, Z may be substituted, preferably with Ar, e.g., phenyl.

In certain embodiments, $R^5$ is hydrogen, Z is absent, L is C=O or $SO_2$, and $R^6$ is selected from Ar—Y and heterocyclyl. In certain preferred such embodiments, heterocyclyl is selected from chromonyl, chromanyl, morpholino, and piperidinyl. In certain other preferred such embodiments, Ar is selected from phenyl, indolyl, benzofuranyl, naphthyl, quinolinyl, quinolonyl, thienyl, pyridyl, pyrazyl, and the like.

In certain embodiments, $R^5$ is hydrogen, L is C=O or $SO_2$, Z is absent, and $R^6$ is $C_{1-6}$alkenyl, where $C_{1-6}$alkenyl is a substituted vinyl group where the substituent is preferably an aryl or heteroaryl group, more preferably a phenyl group optionally substituted with one to four substituents.

In certain embodiments, $R^5$ is hydrogen, L is C=O, Z is $C_{1-6}$alkyl, preferably methylene, and $R^6$ is heterocyclyl. In certain embodiments, $R^6$ is morpholino.

In certain embodiments, at least one of $R^1$, $R^2$ or $R^3$ is heteroaryl, $C_{1-6}$heteroaralkyl, heterocyclyl, or $C_{1-6}$heterocycloalkyl.

In certain embodiments, $R^7$ and $R^8$ are independently selected from hydrogen and $C_{1-6}$alkyl. In certain preferred such embodiments, $R^7$ and $R^8$ are independently selected from hydrogen and methyl. In more preferred such embodiments, $R^7$ and $R^8$ are both hydrogen.

In certain embodiments, a compound of formula (XIII) or formula (XIV) has the following stereochemistry

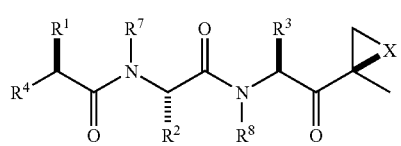

(XIII)

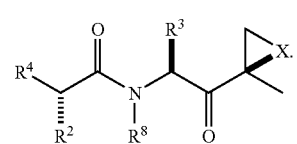

(XIV)

In preferred embodiments, the inhibitor has a structure of formula (XV) or formula (XVIII) or a pharmaceutically acceptable salt thereof:

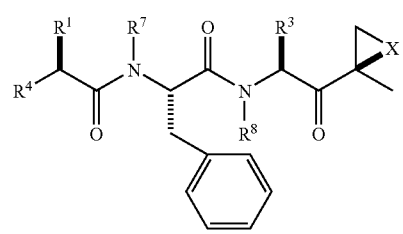

(XV)

-continued

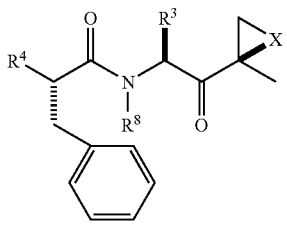
(XVI)

where:
each Ar is independently an aromatic or heteroaromatic group optionally substituted with 1-4 substituents;
L is selected from C=O, C=S, and $SO_2$, preferably $SO_2$ or C=O;
X is selected from O, S, NH, and N—$C_{1-6}$alkyl, preferably O;
Y is absent or is selected from C=O and $SO_2$;
Z is absent or is $C_{1-6}$alkyl;
$R^1$ and $R^3$ are each independently selected from $C_{1-6}$alkyl, $C_{1-6}$hydroxyalkyl, $C_{1-6}$alkoxyalkyl, and aryl, any of which is optionally substituted with one or more of amide, amine, carboxylic acid (or a salt thereof), ester (including $C_{1-5}$ alkyl ester and aryl ester), thiol, or thioether substituents;
$R^4$ is $N(R^5)$L-Z—$R^6$;
$R^5$ is selected from hydrogen, OH, $C_{1-6}$aralkyl, and $C_{1-6}$alkyl, preferably hydrogen;
$R^6$ is selected from hydrogen, $C_{1-6}$alkenyl, Ar—Y—, carbocyclyl, and heterocyclyl; and
$R^7$ and $R^8$ are independently selected from hydrogen, $C_{1-6}$alkyl, and $C_{1-6}$aralkyl, preferably hydrogen.

In certain embodiments, X is O and $R^1$ and $R^3$ are each independently selected from $C_{1-6}$alkyl, $C_{1-6}$hydroxyalkyl, and $C_{1-6}$aralkyl. In preferred such embodiments, $R^1$ and $R^3$ are independently $C_{1-6}$alkyl. In more preferred such embodiments, $R^1$ and $R^3$ are isobutyl.

In certain embodiments, $R^5$ is hydrogen, L is C=O or $SO_2$, and $R^6$ is Ar—Y—, each Ar is independently selected from phenyl, indolyl, benzofuranyl, naphthyl, quinolinyl, quinolonyl, thienyl, pyridyl, pyrazyl, and the like. In certain such embodiments, Ar may be substituted with Ar—Q—, where Q is selected from a direct bond, —O—, and $C_{1-6}$alkyl. In certain other such embodiments where Z is $C_{1-6}$alkyl, Z may be substituted, e.g., preferably with Ar, more preferably with phenyl.

In certain embodiments, $R^5$ is hydrogen, Z is absent, L is C=O or $SO_2$, and $R^6$ is selected from Ar—Y and heterocyclyl. In certain preferred such embodiments, heterocyclyl is selected from chromonyl, chromanyl, morpholino, and piperidinyl. In certain other preferred such embodiments Ar is selected from phenyl, indolyl, benzofuranyl, naphthyl, quinolinyl, quinolonyl, thienyl, pyridyl, pyrazyl, and the like.

In certain embodiments, $R^5$ is hydrogen, L is C=O or $SO_2$, Z is absent, and $R^6$ is $C_{1-6}$alkenyl, where $C_{1-6}$alkenyl is a substituted vinyl group where the substituent is preferably an aryl or heteroaryl group, more preferably the substituent is a phenyl group optionally substituted with one to four substituents.

In certain embodiments, $R^5$ is hydrogen, L is C=O, Z is $C_{1-6}$alkyl, preferably methylene, and $R^6$ is heterocyclyl. In certain embodiments, $R^6$ is morpholino.

In certain embodiments, $R^7$ and $R^8$ are independently selected from hydrogen and $C_{1-6}$alkyl. In certain preferred such embodiments, $R^7$ and $R^8$ are independently selected from hydrogen and methyl. In more preferred such embodiments, $R^7$ and $R^8$ are both hydrogen.

In certain embodiments, -L-Z—$R^6$ is selected from

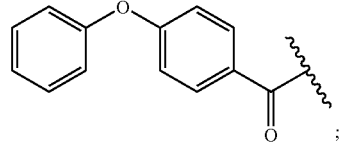

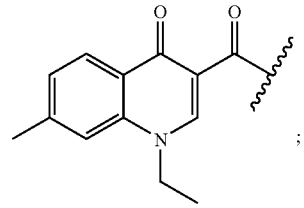

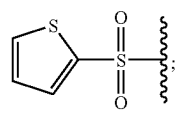

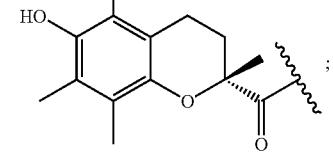

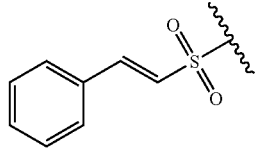

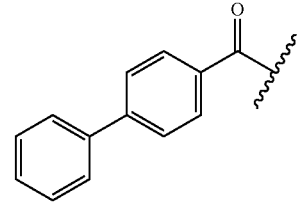

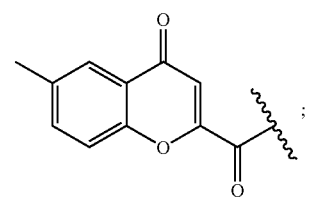

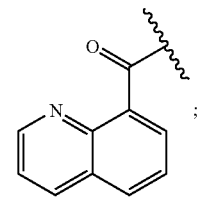

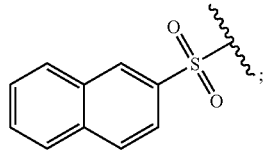

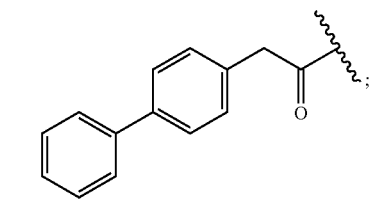

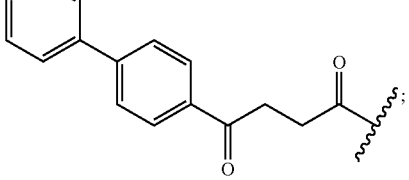

-continued

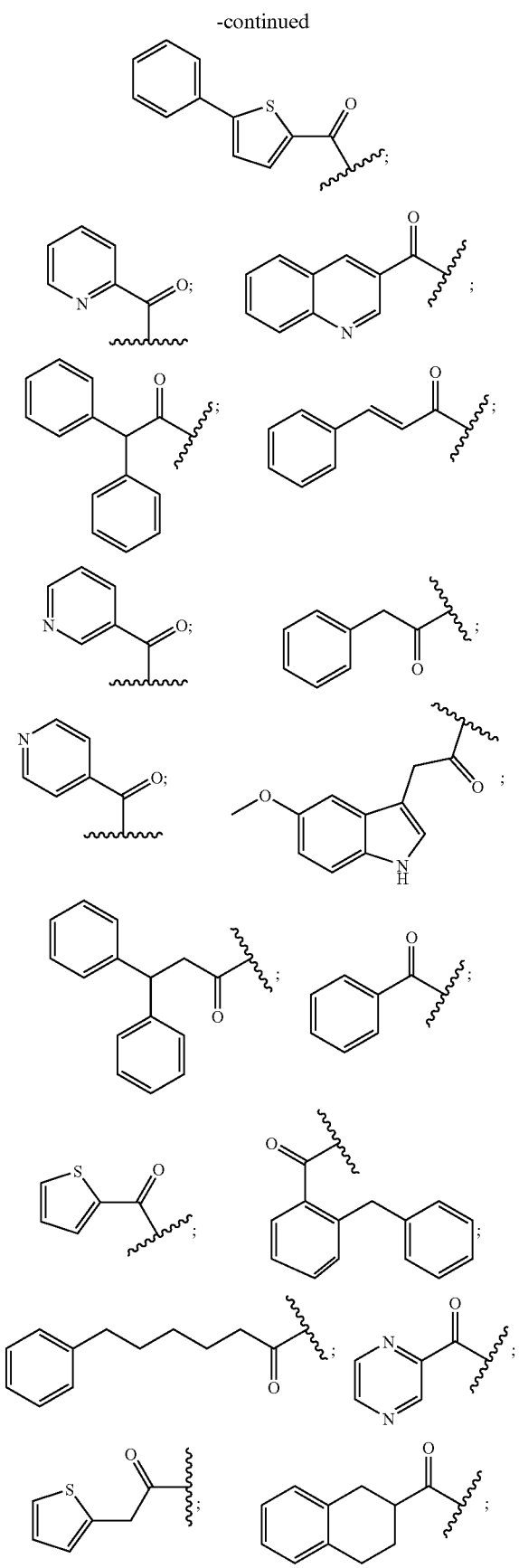
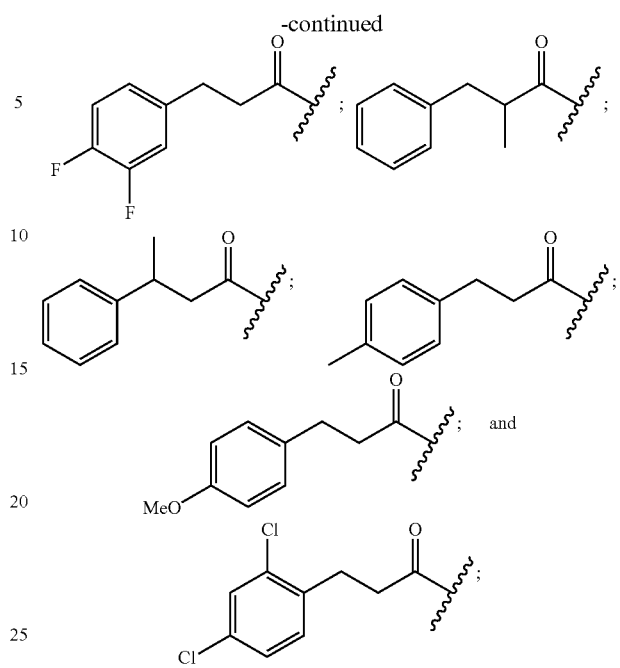

In embodiments including such groups bonded to α' carbons, the stereochemistry of the α'-carbon (that carbon forming a part of the epoxide or aziridine ring) can be (R) or (S). The invention is based, in part, on the structure-function information disclosed herein, which suggests the following preferred stereochemical relationships. Note that a preferred compound may have a number of stereo centers having the indicated up-down (or β-α, where β as drawn herein is above the plane of the page) or (R)-(S) relationship (that is, it is not required that every stereocenter in the compound conform to the preferences stated). In some preferred embodiments, the stereochemistry of the α' carbon is (R), that is, the X atom is β, or above the plane of the molecule.

In certain embodiments inhibitors of the invention may have asymmetric centers that may have either (R) or (S) stereochemistry. The invention is based, in part, on the structure-function information disclosed herein, which suggests the following preferred stereochemical relationships. Note that a preferred compound may have a number of stereocenters having the indicated up-down (or β-α, where β as drawn herein is above the plane of the page) or (R)-(S) relationship (that is, it is not required that every stereocenter in the compound conform to the preferences stated). In some preferred embodiments, the stereochemistry of the α' carbon is (R), that is, the X atom is β, or above the plane of the molecule.

Medical Devices

One aspect of the invention relates to a medical device including composition disclosed herein that include an inhibitor having a structure of formula (I)-(XIV). In one embodiment, the composition is incorporated within a medical device. In certain embodiments, the medical device is a gel comprising a polymer matrix or ceramic matrix and an inhibitor. Said polymer can be either naturally occurring or synthetic. In another embodiment, said gel serves as a drug depot, an adhesive, a suture, a barrier or a sealant.

Another aspect of the invention relates to a medical device comprising a substrate having a surface onto which a composition of the invention is disposed. In one embodiment, the inhibitor is directly disposed on a medical device. In another embodiment, a coating is so disposed, the coating comprising a polymer matrix or ceramic matrix with a composition of the invention dispersed or dissolved therein.

In one embodiment, the medical device is a coronary, vascular, peripheral, or biliary stent. More particularly, the stent of the present invention is an expandable stent. When coated with a matrix containing a composition of the invention, the matrix is flexible to accommodate compressed and expanded states of such an expandable stent. In another embodiment of this invention, the stent has at least a portion which is insertable or implantable into the body of a patient, wherein the portion has a surface which is adapted for exposure to body tissue and wherein at least a part of the surface is coated with a composition of the invention, or a coating comprising a matrix having a composition of the invention is dispersed or dissolved therein. An example of a suitable stent is disclosed in U.S. Pat. No. 4,733,665, which is incorporated herein by reference in its entirety.

In another embodiment, the medical device of the present invention is a surgical implement such as a vascular implant, an intraluminal device, surgical sealant or a vascular support. More particularly, the medical device of the present invention is a catheter, an implantable vascular access port, a central venous catheter, an arterial catheter, a vascular graft, an intraaortic balloon pump, a suture, a ventricular assist pump, a drug-eluting barrier, an adhesive, a vascular wrap, an extra/perivascular support, a blood filter, or a filter adapted for deployment in a blood vessel, coated with a composition of the invention either directly or by a matrix containing a composition of the invention.

In certain embodiments, the intraluminal medical device is coated with a composition of the invention or a coating comprising biologically tolerated matrix and a composition of the invention dispersed in the polymer, said device having an interior surface and an exterior surface, having the coating applied to at least a part of the interior surface, the exterior surface, or both.

In certain embodiments, the medical device may be useful to prevent restenosis after angioplasty. The medical device may also be useful for the treatment of various diseases and conditions by providing localized administration of a composition of the invention. Such diseases and conditions include restenosis, inflammation, rheumatoid arthritis, tissue injury due to inflammation, hyperproliferative diseases, severe or arthritic psoriasis, muscle-wasting diseases, chronic infectious diseases, abnormal immune response, conditions involving vulnerable plaques, injuries related to ischemic conditions, and viral infection and proliferation. Examples of diseases and conditions that are subject to a treatment including the drug coated medical devices of the present invention include atherosclerosis, acute coronary syndrome, Alzheimer's disease, cancer, fever, muscle disuse (atrophy), denervation, vascular occlusions, stroke, HIV infection, nerve injury, renal failure associated with acidosis, and hepatic failure. See, e.g., Goldberg, U.S. Pat. No. 5,340,736.

DEFINITIONS

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkoxy" refers to an alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$alkoxyalkyl" refers to a $C_{1-6}$alkyl group substituted with an alkoxy group, thereby forming an ether.

The term "$C_{1-6}$aralkyl", as used herein, refers to a $C_{1-6}$alkyl group substituted with an aryl group.

The terms "amine" and "amino" are art-recognized and refer to both unsubstituted and substituted amines and salts thereof, e.g., a moiety that can be represented by the general formulae:

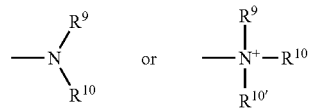

where $R^9$, $R_{10}$ and $R^{10'}$ each independently represent a hydrogen, an alkyl, an alkenyl, —$(CH_2)_m$—$R^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocyclyl or a polycyclyl; and m is zero or an integer from 1 to 8. In preferred embodiments, only one of $R^9$ or $R^{10}$ can be a carbonyl, e.g., $R^9$, $R^{10}$, and the nitrogen together do not form an imide. In even more preferred embodiments, $R^9$ and $R^{10}$ (and optionally $R^{10'}$) each independently represent a hydrogen, an alkyl, an alkenyl, or —$(CH_2)_m$—$R^8$. In certain embodiments, an amino group is basic, meaning its protonated form has a p$K_a$ above 7.00.

The terms "amide" and "amido" are art-recognized as an amino-substituted carbonyl and includes a moiety that can be represented by the general formula:

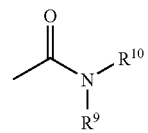

wherein $R^9$, $R^{10}$ are as defined above. Preferred embodiments of the amide will not include imides which may be unstable.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "buffer" is a substance which by its presence in solution increases the amount of acid or alkali that must be added to cause unit change in pH. Thus, a buffer is a substance that assists in regulating the pH of a composition. Typically, a buffer is chosen based upon the desired pH and compatibility with other components of a composition. In general, a buffer has a $pK_a$ that is no more than 1unit less than or greater than the desired pH of the composition (or that the composition will produce upon dissolution).

The terms "carbocycle" and "carbocyclyl", as used herein, refer to a non-aromatic substituted or unsubstituted ring in which each atom of the ring is carbon. The terms "carbocycle" and "carbocyclyl" also include polycyclic ring systems having two or more cyclic rings in which two or more carbons are common to two adjoining rings wherein at least one of the rings is carbocyclic, e.g., the other cyclic rings can be cycloalkyls, cycloalkenyls, cycloalkynyls, aryls, heteroaryls, and/or heterocyclyls.

The term "carbonyl" is art-recognized and includes such moieties as can be represented by the general formula:

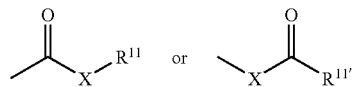

wherein X is a bond or represents an oxygen or a sulfur, and $R^{11}$ represents a hydrogen, an alkyl, an alkenyl, $-(CH_2)_m-R^8$ or a pharmaceutically acceptable salt, $R^{11'}$ represents a hydrogen, an alkyl, an alkenyl or $-(CH_2)_m-R^8$, where m and $R^8$ are as defined above. Where X is an oxygen and $R^{11}$ or $R^{11'}$ is not hydrogen, the formula represents an "ester". Where X is an oxygen, and $R^{11}$ is a hydrogen, the formula represents a "carboxylic acid".

As used herein, "enzyme" can be any partially or wholly proteinaceous molecule which carries out a chemical reaction in a catalytic manner. Such enzymes can be native enzymes, fusion enzymes, proenzymes, apoenzymes, denatured enzymes, farnesylated enzymes, ubiquitinated enzymes, fatty acylated enzymes, gerangeranylated enzymes, GPI-linked enzymes, lipid-linked enzymes, prenylated enzymes, naturally-occurring or artificially-generated mutant enzymes, enzymes with side chain or backbone modifications, enzymes having leader sequences, and enzymes complexed with non-proteinaceous material, such as proteoglycans, proteoliposomes. Enzymes can be made by any means, including natural expression, promoted expression, cloning, various solution-based and solid-based peptide syntheses, and similar methods known to those of skill in the art.

The term "$C_{1-6}$heteroaralkyl", as used herein, refers to a $C_{1-6}$alkyl group substituted with a heteroaryl group.

The term "heteroaryl" includes substituted or unsubstituted aromatic 5- to 7-membered ring structures, more preferably 5- to 6-membered rings, whose ring structures include one to four heteroatoms. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, triazole, pyrazole, pyridine, pyrazine, pyridazine and pyrimidine, and the like.

The term "heteroatom" as used herein means an atom of any element other than carbon or hydrogen. Preferred heteroatoms are nitrogen, oxygen, phosphorus, and sulfur.

The term "heterocyclyl" or "heterocyclic group" refers to substituted or unsubstituted non-aromatic 3- to 10-membered ring structures, more preferably 3- to 7-membered rings, whose ring structures include one to four heteroatoms. The term "heterocyclyl" or "heterocyclic group" also includes polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "$C_{1-6}$hydroxyalkyl" refers to a $C_{1-6}$alkyl group substituted with a hydroxy group.

As used herein, the term "inhibitor" is meant to describe a compound that blocks or reduces an activity of an enzyme (for example, inhibition of proteolytic cleavage of standard fluorogenic peptide substrates such as suc-LLVY-AMC, Box-LLR-AMC and Z-LLE-AMC, inhibition of various catalytic activities of the 20S proteasome). An inhibitor can act with competitive, uncompetitive, or noncompetitive inhibition. An inhibitor can bind reversibly or irreversibly, and therefore the term includes compounds that are suicide substrates of an enzyme. An inhibitor can modify one or more sites on or near the active site of the enzyme, or it can cause a conformational change elsewhere on the enzyme.

As used herein, the term "peptide" includes not only standard amide linkage with standard α-substituents, but commonly utilized peptidomimetics, other modified linkages, non-naturally occurring side chains, and side chain modifications, as detailed herein.

The terms "polycyclyl" or "polycyclic" refer to two or more rings (e.g., cycloalkyls, cycloalkenyls, cycloalkynyls, aryls, heteroaryls, and/or heterocyclyls) in which two or more carbons are common to two adjoining rings, e.g., the rings are "fused rings". Each of the rings of the polycycle can be substituted or unsubstituted.

The term "practically insoluble" refers to proteasome inhibitors that generally have a solubility of less than 0.1 mg/mL in water. The invention also encompasses proteasome inhibitors having a water solubility of less than 0.05 mg/mL and even less than 0.01 mg/mL.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "proteasome" as used herein is meant to include immuno- and constitutive proteasomes.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulffhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment, refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "thioether" refers to an alkyl group, as defined above, having a sulfur moiety attached thereto. In preferred embodiments, the "thioether" is represented by —S— alkyl. Representative thioether groups include methylthio, ethylthio, and the like.

As used herein, the term "treating" or "treatment" includes reversing, reducing, or arresting the symptoms, clinical signs, and underlying pathology of a condition in manner to improve or stabilize a subject's condition.

Uses of Compositions

The biological consequences of proteasome inhibition are numerous. Proteasome inhibition has been suggested as a prevention and/or treatment of a multitude of diseases including, but not limited to, proliferative diseases, neurotoxic/degenerative diseases, Alzheimer's, ischemic conditions, inflammation, auto-immune diseases, HIV, cancers, organ graft rejection, septic shock, inhibition of antigen presentation, decreasing viral gene expression, parasitic infections, conditions associated with acidosis, macular degeneration, pulmonary conditions, muscle wasting diseases, fibrotic diseases, bone and hair growth diseases. Therefore, pharmaceutical formulations for very potent, proteasome-specific compounds, such as the epoxy ketone class of molecules, provide a means of administering the drug to the patient and treating these conditions.

At the cellular level, the accumulation of polyubiquitinated proteins, cell morphological changes, and apoptosis have been reported upon treatment of cells with various proteasome inhibitors. Proteasome inhibition has also been suggested as a possible antitumor therapeutic strategy. The fact that epoxomicin was initially identified in a screen for antitumor compounds validates the proteasome as an antitumor chemotherapeutic target. Accordingly, these compositionsf are useful for treating cancer. Proteasome inhibition has also been associated with inhibition of NF-κB activation and stabilization of p53 levels. Thus, compositions of the invention may also be used to inhibit NF-κB activation, and stabilize p53 levels in cell culture. Since NF-κB is a key regulator of inflammation, it is an attractive target for anti-inflammatory therapeutic intervention. Thus, compositions of the invention may be useful for the treatment of conditions associated with inflammation, including, but not limited to COPD, psoriasis, bronchitis, emphysema, and cystic fibrosis.

The disclosed compositions can be used to treat conditions mediated directly by the proteolytic function of the proteasome such as muscle wasting, or mediated indirectly via proteins which are processed by the proteasome such as NF-κB. The proteasome participates in the rapid elimination and post-translational processing of proteins (e.g., enzymes) involved in cellular regulation (e.g., cell cycle, gene transcription, and metabolic pathways), intercellular communication, and the immune response (e.g., antigen presentation). Specific examples discussed below include β-amyloid protein and regulatory proteins such as cyclins and transcription factor NF-κB.

Another embodiment of the invention is the use of the compositions disclosed herein for the treatment of neurodegenerative diseases and conditions, including, but not limited to, stroke, ischemic damage to the nervous system, neural trauma (e.g., percussive brain damage, spinal cord injury, and traumatic damage to the nervous system), multiple sclerosis and other immune-mediated neuropathies (e.g., Guillain-Barre syndrome and its variants, acute motor axonal neuropathy, acute inflammatory demyelinating polyneuropathy, and Fisher Syndrome), HIV/AIDS dementia complex, axonomy, diabetic neuropathy, Parkinson's disease, Huntington's disease, multiple sclerosis, bacterial, parasitic, fungal, and viral meningitis, encephalitis, vascular dementia, multi-infarct dementia, Lewy body dementia, frontal lobe dementia such as Pick's disease, subcortical dementias (such as Huntington or progressive supranuclear palsy), focal cortical atrophy syndromes (such as primary aphasia), metabolic-toxic dementias (such as chronic hypothyroidism or B12 deficiency), and dementias caused by infections (such as syphilis or chronic meningitis).

Alzheimer's disease is characterized by extracellular deposits of β-amyloid protein (β-AP) in senile plaques and cerebral vessels. β-AP is a peptide fragment of 39 to 42 amino acids derived from an amyloid protein precursor (APP). At least three isoforms of APP are known (695, 751, and 770 amino acids). Alternative splicing of mRNA generates the isoforms; normal processing affects a portion of the β-AP sequence, thereby preventing the generation of β-AP. It is believed that abnormal protein processing by the proteasome contributes to the abundance of β-AP in the Alzheimer brain. The APP-processing enzyme in rats contains about ten different subunits (22 kDa-32 kDa). The 25 kDa subunit has an N-terminal sequence of X-Gln-Asn-Pro-Met-X-Thr-Gly-Thr-Ser, which is identical to the β-subunit of human macropain (Kojima, S. et al., *Fed. Eur. Biochem. Soc.*, (1992) 304: 57-60). The APP-processing enzyme cleaves at the $Gln^{15}$--$Lys^{16}$ bond; in the presence of calcium ion, the enzyme also cleaves at the Met-$^{1}$--$Asp^{1}$ bond, and the $Asp^{1}$--$Ala^{2}$ bonds to release the extracellular domain of β-AP.

One embodiment, therefore, is a method of treating Alzheimer's disease, including administering to a subject an effective amount of a composition disclosed herein. Such treatment includes reducing the rate of β-AP processing, reducing the rate of β-AP plaque formation, reducing the rate of β-AP generation, and reducing the clinical signs of Alzheimer's disease.

Other embodiments of the invention relate to cachexia and muscle-wasting diseases. The proteasome degrades many proteins in maturing reticulocytes and growing fibroblasts. In cells deprived of insulin or serum, the rate of proteolysis nearly doubles. Inhibiting the proteasome reduces proteolysis, thereby reducing both muscle protein loss and the nitrogenous load on kidneys or liver. Inhibitors of the invention are useful for treating conditions such as cancer, chronic infectious diseases, fever, muscle disuse (atrophy) and denervation, nerve injury, fasting, renal failure associated with acidosis, and hepatic failure. See, e.g., Goldberg, U.S. Pat. No. 5,340,736. Embodiments of the invention therefore encompass methods for: reducing the rate of muscle protein degradation in a cell; reducing the rate of intracellular protein degradation; reducing the rate of degradation of p53 protein in a cell; and inhibiting the growth of p53-related cancers. Each of these methods includes contacting a cell (in vivo or in vitro, e.g., a muscle in a subject) with an effective amount of a pharmaceutical composition disclosed herein.

Fibrosis is the excessive and persistent formation of scar tissue resulting from the hyperproliferative growth of fibroblasts and is associated with activation of the TGF-β signaling pathway. Fibrosis involves extensive deposition of extracellular matrix and can occur within virtually any tissue or across several different tissues. Normally, the level of intracellular signaling protein (Smad) that activate transcription of target genes upon TGF-β stimulation is regulated by proteasome activity (Xu et al., 2000). However, accelerated degradation of the TGF-β signaling components has been observed in cancers and other hyperproliferative conditions. Thus, certain embodiments of the invention relate to a method for treating hyperproliferative conditions such as diabetic retinopathy, macular degeneration, diabetic nephropathy, glomerulosclerosis, IgA nephropathy, cirrhosis, biliary atresia, congestive heart failure, scleroderma, radiation-induced fibrosis, and lung fibrosis (idiopathic pulmonary fibrosis, collagen vascular disease, sarcoidosis, interstitial lung diseases and extrinsic lung disorders). The treatment of burn victims is often hampered by fibrosis, thus, an additional embodiment of the invention is the topical or systemic administration of the inhibitors to treat burns. Wound closure following surgery is often associated with disfiguring scars, which may be prevented by inhibition of fibrosis. Thus, in certain embodiments, the invention relates to a method for the prevention or reduction of scarring.

Another protein processed by the proteasome is NF-κB, a member of the Rel protein family. The Rel family of transcriptional activator proteins can be divided into two groups. The first group requires proteolytic processing, and includes p50 (NF-κB1, 105 kDa) and p52 (NF-κ2, 100 kDa). The second group does not require proteolytic processing, and includes p65 (RelA, Rel (c-Rel), and RelB). Both homo- and heterodimers can be formed by Rel family members; NF-κB, for example, is a p50-p65 heterodimer. After phosphorylation and ubiquitination of IκB and p105, the two proteins are degraded and processed, respectively, to produce active NF-κB which translocates from the cytoplasm to the nucleus. Ubiquitinated p105 is also processed by purified proteasomes (Palombella et al., *Cell* (1994) 78:773-785). Active NF-κB forms a stereospecific enhancer complex with other transcriptional activators and, e.g., HMG I(Y), inducing selective expression of a particular gene.

NF-κB regulates genes involved in the immune and inflammatory response, and mitotic events. For example, NF-κB is required for the expression of the immunoglobulin light chain κ gene, the IL-2 receptor α-chain gene, the class I major histocompatibility complex gene, and a number of cytokine genes encoding, for example, IL-2, IL-6, granulocyte colony-stimulating factor, and IFN-β (Palombella et al., *Cell* (1994) 78:773-785). Some embodiments of the invention include methods of affecting the level of expression of IL-2, MHC-I, IL-6, TNFα, IFN-β, or any of the other previously-mentioned proteins, each method including administering to a subject an effective amount of a composition disclosed herein. Complexes including p50 are rapid mediators of acute inflammatory and immune responses (Thanos, D. and Maniatis, T., *Cell* (1995) 80:529-532).

NF-κB also participates in the expression of the cell adhesion genes that encode E-selectin, P-selectin, ICAM, and VCAM-1 (Collins, T., *Lab. Invest.* (1993) 68:499-508). One embodiment of the invention is a method for inhibiting cell adhesion (e.g., cell adhesion mediated by E-selectin, P-selectin, ICAM, or VCAM-1), including contacting a cell with (or administering to a subject) an effective amount of a pharmaceutical composition disclosed herein.

Ischemia and reperfusion injury results in hypoxia, a condition in which there is a deficiency of oxygen reaching the tissues of the body. This condition causes increased degradation of Iκ-Bα, thereby resulting in the activation of NF-κB (Koong et al., 1994). It has been demonstrated that the severity of injury resulting in hypoxia can be reduced with the administration of a proteasome inhibitor (Gao et al., 2000; Bao et al., 2001; Pye et al., 2003). Therefore, certain embodiments of the invention relate to a method of treating an ischemic condition or reperfusion injury comprising administering to a subject in need of such treatment an effective amount of a compound disclosed herein. Examples of such conditions or injuries include, but are not limited to, acute coronary syndrome (vulnerable plaques), arterial occlusive disease (cardiac, cerebral, peripheral arterial and vascular occlusions), atherosclerosis (coronary sclerosis, coronary artery disease), infarctions, heart failure, pancreatitis, myocardial hypertrophy, stenosis, and restenosis.

NF-κB also binds specifically to the HIV-enhancer/promoter. When compared to the Nef of mac239, the HIV regulatory protein Nef of pbj14 differs by two amino acids in the region which controls protein kinase binding. It is believed that the protein kinase signals the phosphorylation of IκB, triggering IκB degradation through the ubiquitin-proteasome pathway. After degradation, NF-κB is released into the nucleus, thus enhancing the transcription of HIV (Cohen, *J., Science,* (1995) 267:960). Two embodiments of the invention are a method for inhibiting or reducing HIV infection in a subject, and a method for decreasing the level of viral gene expression, each method including administering to the subject an effective amount of a composition disclosed herein.

Overproduction of lipopolysaccharide (LPS)-induced cytokines such as TNFα is considered to be central to the processes associated with septic shock. Furthermore, it is generally accepted that the first step in the activation of cells by LPS is the binding of LPS to specific membrane receptors. The α- and β-subunits of the 20S proteasome complex have been identified as LPS-binding proteins, suggesting that the LPS-induced signal transduction may be an important therapeutic target in the treatment or prevention of sepsis (Qureshi, N. et al., *J. Immun.* (2003) 171: 1515-1525). Therefore, in certain embodiments, compositions of the invention may be used for the inhibition of TNFα to prevent and/or treat septic shock.

Intracellular proteolysis generates small peptides for presentation to T-lymphocytes to induce MHC class I-mediated immune responses. The immune system screens for autologous cells that are virally infected or have undergone oncogenic transformation. One embodiment is a method for inhibiting antigen presentation in a cell, including exposing the cell to a composition described herein. A further embodiment is a method for suppressing the immune system of a subject (e.g., inhibiting transplant rejection, allergy, asthma), including administering to the subject an effective amount of a composition described herein. Compositions of the invention can also be used to treat autoimmune diseases such as lupus, rheumatoid arthritis, multiple sclerosis, and inflammatory bowel diseases such as ulcerative colitis and Crohn's disease.

Another further embodiment is a method for altering the repertoire of antigenic peptides produced by the proteasome or other Ntn with multicatalytic activity. For example, if the PGPH activity of 20S proteasome is selectively inhibited, a different set of antigenic peptides will be produced by the proteasome and presented in MHC molecules on the surfaces of cells than would be produced and presented either without any enzyme inhibition, or with, for example, selective inhibition of chymotrypsin-like activity of the proteasome.

Certain proteasome inhibitors block both degradation and processing of ubiquitinated NF-κB in vitro and in vivo. Proteasome inhibitors also block IκB-α degradation and NF-κB activation (Palombella, et al. *Cell* (1994) 78:773-785; and Traenckner, et al., *EMBO J.* (1994) 13:5433-5441). One embodiment of the invention is a method for inhibiting IκB-α degradation, including contacting the cell with a composition described herein. A further embodiment is a method for reducing the cellular content of NF-κB in a cell, muscle, organ, or subject, including contacting the cell, muscle, organ, or subject with a composition described herein.

Other eukaryotic transcription factors that require proteolytic processing include the general transcription factor TFIIA, herpes simplex virus VP16 accessory protein (host cell factor), virus-inducible IFN regulatory factor 2 protein, and the membrane-bound sterol regulatory element-binding protein 1.

Other embodiments of the invention are methods for affecting cyclin-dependent eukaryotic cell cycles, including exposing a cell (in vitro or in vivo) to a composition disclosed herein. Cyclins are proteins involved in cell cycle control. The proteasome participates in the degradation of cyclins. Examples of cyclins include mitotic cyclins, G1 cyclins, and cyclin B. Degradation of cyclins enables a cell to exit one cell cycle stage (e.g., mitosis) and enter another (e.g., division). It is believed all cyclins are associated with $p34^{cdc2}$ protein kinase or related kinases. The proteolysis targeting signal is localized to amino acids 42-RAALGNISEN-50 (destruction box). There is evidence that cyclin is converted to a form vulnerable to a ubiquitin ligase or that a cyclin-specific ligase is activated during mitosis (Ciechanover, A., *Cell*, (1994) 79:13-21). Inhibition of the proteasome inhibits cyclin degradation, and therefore inhibits cell proliferation, for example, in cyclin-related cancers (Kumatori et al., Proc. Natl. Acad. Sci. USA (1990) 87:7071-7075). One embodiment of the invention is a method for treating a proliferative disease in a subject (e.g., cancer, psoriasis, or restenosis), including administering to the subject an effective amount of a composition disclosed herein. The invention also encompasses a method for treating cyclin-related inflammation in a subject, including adminstering to a subject a therapeutically effective amount of a composition described herein.

Additional embodiments are methods for affecting the proteasome-dependent regulation of oncoproteins and methods of treating or inhibiting cancer growth, each method including exposing a cell (in vivo, e.g., in a subject, or in vitro) to a composition disclosed herein. HPV-16 and HPV-18-derived E6 proteins stimulate ATP- and ubiquitin-dependent conjugation and degradation of p53 in crude reticulocyte lysates. The recessive oncogene p53 has been shown to accumulate at the nonpermissive temperature in a cell line with a mutated thermolabile E1. Elevated levels of p53 may lead to apoptosis. Examples of proto-oncoproteins degraded by the ubiquitin system include c-Mos, c-Fos, and c-Jun. One embodiment is a method for treating p53-related apoptosis, including administering to a subject an effective amount of a composition disclosed herein.

In another embodiment, the disclosed compositions are useful for the treatment of a parasitic infection, such as infections caused by protozoan parasites. The proteasome of these parasites is considered to be involved primarily in cell differentiation and replication activities (Paugam et al., Trends Parasitol. 2003, 19(2): 55-59). Furthermore, entamoeba species have been shown to lose encystation capacity when exposed to proteasome inhibitors (Gonzales, et al., Arch. Med. Res. 1997, 28, Spec No: 139-140). In certain such embodiments, the disclosed compositions are useful for the treatment of parasitic infections in humans caused by a protozoan parasite selected from *Plasmodium* sps. (including *P. falciparum, P. vivax, P. malariae*, and *P. ovale*, which cause malaria), *Trypanosoma* sps. (including *T. cruzi*, which causes Chagas' disease, and *T. brucei* which causes African sleeping sickness), *Leishmania* sps. (including *L. amazonesis, L. donovani, L. infantum, L. mexicana*, etc.), *Pneumocystis carinii* (a protozoan known to cause pneumonia in AIDS and other immunosuppressed patients), *Toxoplasma gondii, Entamoeba histolytica, Entamoeba invadens*, and *Giardia lamblia*. In certain embodiments, the disclosed compositions are useful for the treatment of parasitic infections in animals and livestock caused by a protozoan parasite selected from *Plasmodium hermani, Cryptosporidium* sps., *Echinococcus granulosus, Eimeria tenella, Sarcocystis neurona*, and *Neurospora crassa*. Other compounds useful as proteasome inhibitors in the treatment of parasitic diseases are described in WO 98/10779, which is incorporated herein in its entirety.

In certain embodiments, the disclosed compositions inhibit proteasome activity irreversibly in a parasite. Such irreversible inhibition has been shown to induce shutdown in enzyme activity without recovery in red blood cells and white blood cells. In certain such embodiments, the long half-life of blood cells may provide prolonged protection with regard to therapy against recurring exposures to parasites. In certain embodiments, the long half-life of blood cells may provide prolonged protection with regard to chemoprophylaxis against future infection.

It has also been demonstrated that inhibitors that bind to the 20S proteasome stimulate bone formation in bone organ cultures. Furthermore, when such inhibitors have been administered systemically to mice, certain proteasome inhibitors increased bone volume and bone formation rates over 70% (Garrett, I. R. et al., *J. Clin. Invest.* (2003) 111: 1771-1782), therefore suggesting that the ubiquitin-proteasome machinery regulates osteoblast differentiation and bone formation. Therefore, the disclosed compositions may be useful in the treatment and/or prevention of diseases associated with bone loss, such as osteroporosis.

Bone tissue is an excellent source for factors which have the capacity for stimulating bone cells. Thus, extracts of bovine bone tissue contain not only structural proteins which are responsible for maintaining the structural integrity of bone, but also biologically active bone growth factors which can stimulate bone cells to proliferate. Among these latter factors are a recently described family of proteins called bone morphogenetic proteins (BMPs). All of these growth factors have effects on other types of cells, as well as on bone cells, including Hardy, M. H., et al., Trans Genet (1992) 8:55-61 describes evidence that bone morphogenetic proteins (BMPs), are differentially expressed in hair follicles during development. Harris, S. E., et al., J Bone Miner Res (1994) 9:855-863 describes the effects of TGF-β on expression of BMP-2 and other substances in bone cells. BMP-2 expression in mature follicles also occurs during maturation and after the period of cell proliferation (Hardy, et al. (1992, supra). Thus, compounds of the invention may also be useful for hair follicle growth stimulation.

Finally, the disclosed compositions are also useful as diagnostic agents (e.g., in diagnostic kits or for use in clinical laboratories) for screening for proteins (e.g., enzymes, transcription factors) processed by Ntn hydrolases, including the proteasome. The disclosed compositions are also useful as research reagents for specifically binding the X/MB1 subunit or α-chain and inhibiting the proteolytic activities associated with it. For example, the activity of (and specific inhibitors of) other subunits of the proteasome can be determined.

Most cellular proteins are subject to proteolytic processing during maturation or activation. Enzyme inhibitors disclosed herein can be used to determine whether a cellular, developmental, or physiological process or output is regulated by the proteolytic activity of a particular Ntn hydrolase. One such method includes obtaining an organism, an intact cell preparation, or a cell extract; exposing the organism, cell preparation, or cell extract to a composition disclosed herein; exposing the compound-exposed organism, cell preparation, or cell extract to a signal, and monitoring the process or output. The high selectivity of the compounds disclosed herein permits rapid and accurate elimination or implication of the Ntn (for example, the 20S proteasome) in a given cellular, developmental, or physiological process.

Administration

Compositions prepared as described herein can be administered in various forms, depending on the disorder to be treated and the age, condition, and body weight of the patient, as is well known in the art. For example, where the compositions are to be administered orally, they may be formulated as tablets, capsules, granules, powders, or syrups; or for parenteral administration, they may be formulated as injections (intravenous, intramuscular, or subcutaneous), drop infusion preparations, or suppositories. For application by the ophthalmic mucous membrane route, they may be formulated as eye drops or eye ointments. These formulations can be prepared by conventional means in conjunction with the methods described herein, and, if desired, the active ingredient may be mixed with any conventional additive or excipient, such as a binder, a disintegrating agent, a lubricant, a corrigent, a solubilizing agent, a suspension aid, an emulsifying agent, or a coating agent in addition to a cyclodextrin and a buffer. Although the dosage will vary depending on the symptoms, age and body weight of the patient, the nature and severity of the disorder to be treated or prevented, the route of administration and the form of the drug, in general, a daily dosage of from 0.01 to 2000 mg of the compound is recommended for an adult human patient, and this may be administered in a single dose or in divided doses. The amount of active ingredient which can be combined with a carrier material to produce a single dosage form will generally be that amount of the compound which produces a therapeutic effect. In general, compositions intended for parenteral use (e.g., intravenous, subcutaneous injection) include a substituted cyclodextrin. Compositions administered via other routes, particularly the oral route, include a substituted or unsubstituted cyclodextrin.

The precise time of administration and/or amount of the composition that will yield the most effective results in terms of efficacy of treatment in a given patient will depend upon the activity, pharmacokinetics, and bioavailability of a particular compound, physiological condition of the patient (including age, sex, disease type and stage, general physical condition, responsiveness to a given dosage, and type of medication), route of administration, etc. However, the above guidelines can be used as the basis for fine-tuning the treatment, e.g., determining the optimum time and/or amount of administration, which will require no more than routine experimentation consisting of monitoring the subject and adjusting the dosage and/or timing.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition, or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose, and sucrose; (2) starches, such as corn starch, potato starch, and substituted or unsubstituted β-cyclodextrin; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salt" refers to the relatively non-toxic, inorganic and organic acid addition salts of the inhibitor(s). These salts can be prepared in situ during the final isolation and purification of the inhibitor(s), or by separately reacting a purified inhibitor(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, laurylsulphonate salts, and amino acid salts, and the like. (See, for example, Berge et al. (1977) "Pharmaceutical Salts", *J. Pharm. Sci.* 66: 1-19.)

In other cases, the inhibitors useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of an inhibitor(s). These salts can likewise be prepared in situ during the final isolation and purification of the inhibitor(s), or by separately reacting the purified inhibitor(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

Wetting agents, emulsifiers, and lubricants, such as sodium lauryl sulfate and magnesium stearate, as well as coloring agents, release agents, coating agents, sweetening, flavoring, and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite, and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert matrix, such as gelatin and glycerin, or sucrose and acacia) and/or as mouthwashes, and the like, each containing a predetermined amount of an inhibitor(s) as an active ingredient. A composition may also be administered as a bolus, electuary, or paste.

In solid dosage forms for oral administration (capsules, tablets, pills, dragees, powders, granules, and the like), the active ingredient is mixed with one or more pharmaceutically acceptable carriers, such as sodium citrate or dicalcium phosphate, and/or any of the following: (1) fillers or extenders, such as starches, cyclodextrins, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols, and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor(s) moistened with an inert liquid diluent.

Tablets, and other solid dosage forms, such as dragees, capsules, pills, and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents, and emulsifiers such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols, and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active inhibitor(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more inhibitor(s) with one or more suitable nonirritating excipients or carriers comprising, for example, cocoa butter, polyethylene glycol, a suppository wax or a salicylate, which is solid at room temperature, but liquid at body temperature and, therefore, will melt in the rectum or vaginal cavity and release the active agent.

Formulations which are suitable for vaginal administration also include pessaries, tampons, creams, gels, pastes, foams, or spray formulations containing such carriers as are known in the art to be appropriate.

Dosage forms for the topical or transdermal administration of an inhibitor(s) include powders, sprays, ointments, pastes, creams, lotions, gels, solutions, patches, and inhalants. The active component may be mixed under sterile conditions with a pharmaceutically acceptable carrier, and with any preservatives, buffers, or propellants which may be required.

The ointments, pastes, creams, and gels may contain, in addition to inhibitor(s), excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to an inhibitor(s), excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane and propane.

The inhibitor(s) can be alternatively administered by aerosol. This is accomplished by preparing an aqueous aerosol, liposomal preparation, or solid particles containing the composition. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular composition, but typically include nonionic surfactants (Tweens, Pluronics, sorbitan esters, lecithin, Cremophors), pharmaceutically acceptable co-solvents such as polyethylene glycol, innocuous proteins like serum albumin, sorbitan esters, oleic acid, lecithin, amino acids such as glycine, buffers, salts, sugars, or sugar alcohols. Aerosols generally are prepared from isotonic solutions.

Transdermal patches have the added advantage of providing controlled delivery of an inhibitor(s) to the body. Such dosage forms can be made by dissolving or dispersing the agent in the proper medium. Absorption enhancers can also be used to increase the flux of the inhibitor(s) across the skin. The rate of such flux can be controlled by either providing a rate controlling membrane or dispersing the inhibitor(s) in a polymer matrix or gel.

Pharmaceutical compositions of this invention suitable for parenteral administration comprise one or more inhibitors(s) in combination with one or more pharmaceutically acceptable sterile aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include tonicity-adjusting agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. For example, delayed absorption of a parenterally administered drug form is accomplished by dissolving or suspending the drug in an oil vehicle.

Injectable depot forms are made by forming microencapsule matrices of inhibitor(s) in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of agents may be given orally, parenterally, topically, or rectally. They are, of course, given by forms suitable for each administration route. For example, they are administered in tablets or capsule form, by injection, inhalation, eye lotion, ointment, suppository, infusion; topically by lotion or ointment; and rectally by suppositories. Oral administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection, and infusion.

The phrases "systemic administration," "administered systemically," "peripheral administration" and "administered peripherally" as used herein mean the administration of a ligand, drug, or other material other than directly into the central nervous system, such that it enters the patient's system and thus, is subject to metabolism and other like processes, for example, subcutaneous administration.

These inhibitors(s) may be administered to humans and other animals for therapy by any suitable route of administration, including orally, nasally, as by, for example, a spray, rectally, intravaginally, parenterally, intracisternally, and topically, as by powders, ointments or drops, including buccally and sublingually.

Regardless of the route of administration selected, the inhibitor(s), which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The concentration of a disclosed compound in a pharmaceutically acceptable mixture will vary depending on several factors, including the dosage of the compound to be administered, the pharmacokinetic characteristics of the compound(s) employed, and the route of administration. In general, the compositions of this invention may be provided in an aqueous solution containing about 0.1-10% w/v of a compound disclosed herein, among other substances, for parenteral administration. Typical dose ranges are from about 0.01 to about 50 mg/kg of body weight per day, given in 1-4 divided doses. Each divided dose may contain the same or different compounds of the invention. The dosage will be an effective amount depending on several factors including the overall health of a patient, and the formulation and route of administration of the selected compound(s).

In a preferred embodiment, the proteasome inhibitor is a dry powder prior to its addition to the cyclodextrin solution. The process of dissolving the drug into the cyclodextrin solution can be enhanced by mixing, stirring or agitation. In the most preferred embodiment the solvent in the cyclodextrin solution is "water for injection" (WFI), meaning that it is purified, sterile and low in endotoxin. This formulation is suitable for both parenteral and oral administration.

In another preferred embodiment, the pharmaceutical composition is an oral solution or a parenteral solution. Another embodiment is a freeze-dried preparation that can be reconstituted prior to administration. As a solid, this formulation may also include tablets, capsules or powders.

Another aspect of the invention provides a conjoint therapy wherein one or more other therapeutic agents are administered with the proteasome inhibitor composition. Such conjoint treatment may be achieved by way of the simultaneous, sequential, or separate dosing of the individual components of the treatment.

In certain embodiments, a composition of the invention is conjointly administered with one or more other proteasome inhibitor(s).

In certain embodiments, a composition of the invention is conjointly administered with a chemotherapeutic. Suitable chemotherapeutics may include, natural products such as vinca alkaloids (i.e. vinblastine, vincristine, and vinorelbine), paclitaxel, epidipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexaamethylmelaamine and thiotepa), alkyl sulfonates (busulfan), nitrosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine); aromatase inhibitors (anastrozole, exemestane, and letrozole); and platinum coordination complexes (cisplatin, carboplatin), procarbazine, hydroxyurea, mitotane, aminoglutethimide; histone deacetylase (HDAC) inhibitors (trichostatin, sodium butyrate, apicidan, suberoyl anilide hydroamic acid); hormones (i.e. estrogen) and hormone agonists such as leutinizing hormone releasing hormone (LHRH) agonists (goserelin, leuprolide and triptorelin). Other chemotherapeutic agents may include mechlorethamine, camptothecin, ifosfamide, tamoxifen, raloxifene, gemcitabine, navelbine, or any analog or derivative variant of the foregoing.

In certain embodiments, a composition of the invention is conjointly administered with a cytokine. Cytokines include, but are not limited to, Interferon-γ, -α, and -β, Interleukins 1-8, 10 and 12, Granulocyte Monocyte Colony-Stimulating factor (GM-CSF), TNF-α and -β, and TGF-β.

In certain embodiments, a composition of the invention is conjointly administered with a steroid. Suitable steroids may include, but are not limited to, 21-acetoxypregnenolone, alclometasone, algestone, amcinonide, beclomethasone, betamethasone, budesonide, chloroprednisone, clobetasol, clocortolone, cloprednol, corticosterone, cortisone, cortivazol, deflazacort, desonide, desoximetasone, dexamethasone, diflorasone, diflucortolone, difuprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisolone sodium phosphate, prednisone, prednival, prednylidene, rimexolone, tixocortol, triamcinolone, triamcinolone acetonide, triamcinolone benetonide, triamcinolone hexacetonide, and salts and/or derivatives thereof.

In certain embodiments, a composition of the invention is conjointly administered with an immunotherapeutic agent. Suitable immunotherapeutic agents may include, but are not limited to, MDR modulators (verapamil, valspordar, biricodar, tariquidar, laniquidar), cyclosporine, thalidomide, and monoclonal antibodies. The monoclonal antibodies can be either naked or conjugated such as rituximab, tositumomab, alemtuzumab, epratuzumab, ibritumomab tiuxetan, gemtuzumab ozogamicin, bevacizumab, cetuximab, erlotinib and trastuzumab.

Preparation Methods

Another aspect of this invention involves the method of preparing a pharmaceutical composition of a proteasome inhibitor. The method comprises determining the desired volume, preparing a cyclodextrin solution comprising the cyclodextrin and the buffer acid in 20% to 90% (e.g., 75%) of the desired final volume of $H_2O$, suspending the appropriate amount of the proteasome inhibitor into the cyclodextrin solution and stirring until dissolved, adjusting the pH (e.g., with a base solution, preferably a sodium hydroxide solution), and then adding enough aqueous diluent to achieve the desired final volume.

A further aspect of this invention involves the method of preparing a pharmaceutical composition of a proteasome inhibitor. The method comprises determining the desired volume, preparing a cyclodextrin solution comprising the cyclodextrin and the buffer base in 20% to 90% (e.g., 75%) of the desired final volume of $H_2O$, suspending the appropriate amount of the proteasome inhibitor into the cyclodextrin solution and stirring until dissolved, adjusting the pH (e.g., with an acid solution), and then adding enough aqueous diluent to achieve the desired final volume.

An alternative method of preparing a pharmaceutical composition of the invention involves dissolving a proteasome inhibitor into an appropriate solvent (e.g., an alcohol such as ethanol), dissolving a cyclodextrin into a miscible, preferably the same, solvent and mixing the two together. The solvent is then removed, such as by rotary evaporation, spray drying, or lyophilization, to obtain a solid. The solid is then dissolved in an appropriate aqueous diluent, and then pH adjusted, if necessary.

There can be a period between obtaining the solid and redissolving it in aqueous buffer. In one example, the solid is sterilized (e.g., to allow storage and/or shipment, generally in a contaminant-free and -proof container) and is dissolved immediately prior to use.

The compositions obtained above are typically sterilized before use, unless the preparation involved a sterilization step and no contamination occurs prior to use.

The proteasome inhibitor dissolved in aqueous buffer, preferably following sterilization, can optionally be lyophilized (in a contaminant-free and -proof container) and reconstituted in appropriate aqueous diluent just prior to use. The preferred diluent being water for injection (WFI).

EXEMPLIFICATION

Example 1

Peptide (b)/HPBCD Formulation

100 μg/mL peptide (b) was formulated in an aqueous solution containing 130 mg/mL hydroxypropyl beta cyclodextrin (HPBCD) and ca. 0.9% (w/v) NaCl. This was a supersaturated (metastable) solution at room temperature and could not be made by simply dissolving peptide (b) in aqueous 13% HPBCD/0.9% (w/v) NaCl.

The desired quantity of peptide (b) was weighed and dissolved in absolute ethanol at a concentration of 1 mg/mL. For each 1 mg of peptide (b) to be formulated, 1.3 g HPBCD was dissolved in absolute ethanol at a concentration of 10 mg/mL. This ethanol/HPBCD solution was then combined with the ethanol/peptide (b) solution, stirred 5 minutes at room temperature and then evaporated under reduced pressure (rotovapped) to yield a white solid. This solid was placed under high vacuum (ca. 1 mTorr) for 24 hrs, pulverized and then placed under high vacuum (ca. 1 mTorr) for another 4 hrs to yield dry solid. The final formulation was prepared by dissolving this solid drug product to a final concentration of 100 μg peptide (b)/mL solid drug product in ice cold USP grade aqueous 0.9% (w/v) NaCl followed by sterile filtration. Room temperature stability of the reconstituted drug product was ca. 12 hrs.

Example 2

Peptide (a)/SBECD Formulation 2 mg/mL peptide (a) was formulated in an aqueous solution containing 10% (w/v) SBECD and 10 mM citric acid adjusted to pH 3.5 with 0.1 M aqueous sodium hydroxide.

Appropriate masses of SBECD and citric acid were added to a volume of WFI corresponding to approximately 75% that of the final formulation. This mixture was then stirred at room temperature until complete dissolution of the SBECD and citric acid was effected. An appropriate mass of peptide (a) was then added and the resulting mixture stirred at room temperature until the added peptide (a) was dissolved. A pH electrode was then immersed in the solution and, with rapid stirring, the pH was adjusted to 3.5 by slow addition of 0.1 M sodium hydroxide in WFI; slow addition of the sodium hydroxide solution with adequate stirring was necessary to prevent precipitation of peptide (a). With rapid stirring, the resulting solution was then diluted with WFI to a final peptide (a) concentration of 2.0 mg/mL. This solution was then sterile filtered to yield the final formulation.

Several other final pH values were used for the peptide (a)/SBECD formulations. FIG. 1 shows the solubility of peptide (a) at various pH values in aqueous 10% (w/v) sulfobutyl ether beta-cyclodextrin (SBECD)/10 mM sodium citrate solutions.

Figure 2:
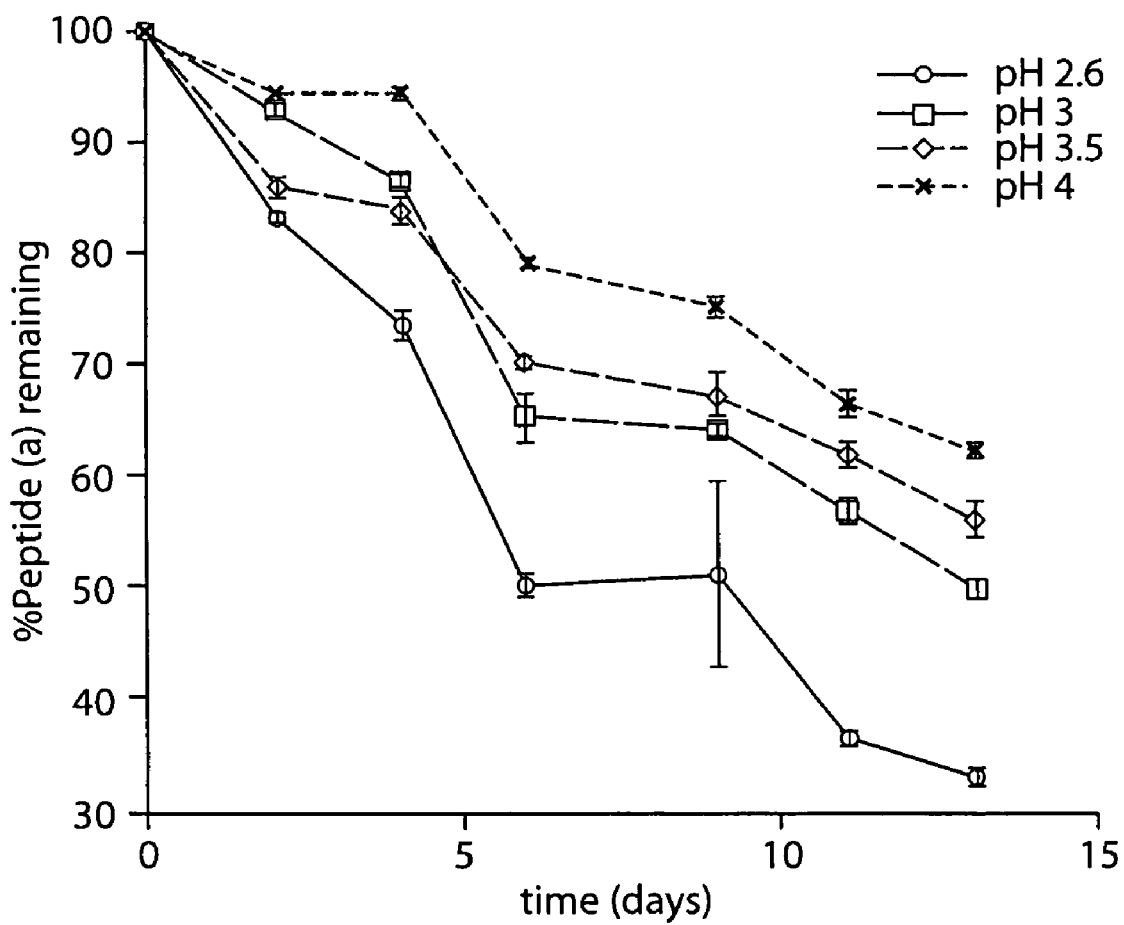
FIG. 2 shows the percentage of peptide (a) remaining in aqueous 10% (w/v) SBECD/10 mM sodium citrate solutions over time at various pH values.

In addition, the stability of peptide (a) in these formulations was determined. FIG. 2 shows the percentage of peptide (a) remaining in aqueous 10% (w/v) SBECD/10 mM sodium citrate solutions over time at various pH values.

Example 3

(3×) Peptide (a)/SBECD Formulation, Lyophilization of Formulation and Reconstitution 6 mg/mL peptide (a) was formulated in an aqueous solution containing 30% (w/v) SBECD and 30 mM citric acid adjusted to pH 3.5 with 0.5 M aqueous sodium hydroxide.

Appropriate masses of SBECD and citric acid were added to a volume of WFI corresponding to 70% that of the final formulation. This mixture was then stirred at room temperature until complete dissolution of the SBECD and citric acid was effected. An appropriate mass of peptide (a) was then added and the resulting mixture stirred at room temperature until the added peptide (a) was dissolved. A pH electrode was then immersed in the solution and, with rapid stirring, the pH was adjusted to 3.5 by slow addition of 0.5 M sodium hydroxide in WFI; slow addition of the sodium hydroxide solution with adequate stirring was necessary to prevent precipitation of peptide (a). With rapid stirring, the resulting solution was then diluted with WFI to a final peptide (a) concentration of 6.0 mg/mL. This solution was then sterile filtered to yield the final formulation.

The vials containing product were loaded onto the shelves and the temperature set for 5° C. for 2 hrs. The shelves were then cooled at a rate of 30° C. per hour to a target set point of −45° C. which was then maintained for 4 hours to complete the freezing. The condenser was set to below −50° C., and the chamber was evacuated to a target pressure of 60 μm Hg. Chamber pressure was controlled by bleeding in 0.2μ filtered Nitrogen, NF into the chamber. The shelves were then warmed to a target setpoint of −18° C. at an average controlled rate of 30° C. per hour and control set at that setpoint to complete the primary drying. The shelves were warmed to a target setpoint of 30° C. at an average controlled rate of 12° C. per hour and control at that setpoint for 12 hrs to complete the secondary drying.

The chamber was then backfilled with 0.2μ filtered Nitrogen, NF followed by stoppering of the product at 1 atm.

Reconstitution was effected by addition of 9.75 mL of WFI, USP to produce the desired fill volume within the vial of 10.5 mL. The vial was inverted several times. The time for dissolution was less than 2 minutes. The vial was then allowed to stand for several minutes to allow the bubbles to rise. A clear colorless solution free of visible particulate matter was produced. The pH measured was 3.5±0.1.

Example 4

Peptide (a)/SBECD Dry Powder Formulation

Peptide (a) was formulated as a cyclodextrin-complexed dry powder for dissolution into 10 mM citric acid prior to IV administration.

Appropriate masses of peptide and SBECD were added to an appropriate volume of anhydrous ethanol to yield an ethanolic solution containing 4 mg/mL peptide (a) and 200 mg/mL SBECD. This solution was sterile filtered (0.2 μm) and then evaporated (under sterile conditions) to dryness at room temperature under reduced pressure to yield a white to off white solid. This solid was then crushed (under sterile conditions) to yield a free-flowing powder. An appropriate mass of this solid was sterile-filled into an appropriately-sized sterile vial. The vial was then sealed with a sterile pierceable elastomer stopper/aluminum flip-off seal container-closure system. An appropriate volume of 10 mM citric acid in WFI (adjusted to pH 3.2 with 0.1 M sodium hydroxide in WFI) was then added via sterile needle and syringe through the pierceable elastomer stopped and agitated at room temperature until all solid material dissolved to yield a final solution containing 2 mg/mL peptide (a), 100 mg/mL SBECD and 10 mM citric acid/sodium citrate buffer pH 3.2-4.0.

EQUIVALENTS

Those skilled in the art will recognize, or be able to ascertain using no more than routine experimentation, numerous equivalents to the compositions and methods of use thereof described herein. Such equivalents are considered to be within the scope of this invention and are covered by the following claims.

All of the above-cited references and publications are hereby incorporated by reference.

What is claimed is:

1. A pharmaceutical composition comprising a practically insoluble peptide epoxy ketone proteasome inhibitor or a pharmaceutically acceptable salt thereof and a substituted cyclodextrin selected from hydroxypropyl beta-cyclodextrin and sulfobutyl ether beta-cyclodextrin (SBECD).

2. The pharmaceutical composition of claim 1, wherein the pharmaceutical composition is a solution.

3. The pharmaceutical composition of claim 2, wherein the solution comprises at least 0.02 mg/mL of the proteasome inhibitor.

4. The pharmaceutical composition of claim 3, wherein the solution comprises at least 0.1 mg/mL of the proteasome inhibitor.

5. The pharmaceutical composition of claim 4, wherein the solution comprises at least 1 mg/mL of the proteasome inhibitor.

6. The pharmaceutical composition of claim 1, wherein the pharmaceutical composition is a water-soluble solid.

7. The pharmaceutical composition of claim 6, wherein the pharmaceutical composition dissolves in water at a concentration of at least 0.02 mg/mL of the proteasome inhibitor.

8. The pharmaceutical composition of claim 7, wherein the pharmaceutical composition dissolves in water at a concentration of at least 0.1 mg/mL of the proteasome inhibitor.

9. The pharmaceutical composition of claim 8, wherein the pharmaceutical composition dissolves in water at a concentration of at least 1 mg/mL of the proteasome inhibitor.

10. The pharmaceutical composition of claim 1, further comprising a buffer.

11. The pharmaceutical composition of claim 10, wherein the buffer is a salt.

12. The pharmaceutical composition of claim 10, wherein the buffer, when the pharmaceutical composition is dissolved in water, achieves a pH at which at least 10% of the inhibitor molecules are ionized.

13. The pharmaceutical composition of claim 12, wherein the buffer, when the pharmaceutical composition is dissolved in water, achieves a pH at which at least 50% of the inhibitor molecules are ionized.

14. The pharmaceutical composition of claim 1, further comprising a pharmaceutically acceptable carrier or diluent.

15. The pharmaceutical composition of claim 1, wherein the proteasome inhibitor is represented by structural formula (II) or a pharmaceutically acceptable salt thereof:

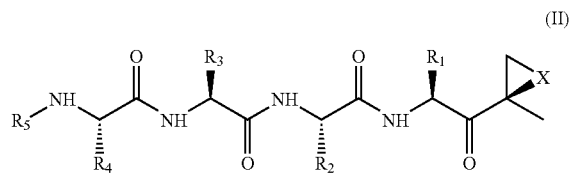

wherein:

X is oxygen;

$R_1$, $R_2$, $R_3$ and $R_4$ are independently selected from $C_{1-6}$alkyl or $C_{1-6}$hydroxy alkyl or $C_{1-6}$alkoxy alkyl, aryl, heteroaryl, $C_{1-6}$heteroaralkyl, heterocyclyl, and $C_{1-6}$heterocycloalkyl, and aryl-substituted $C_{1-6}$alkyl, wherein such groups are optionally substituted with one or more amide linkages, amines, carboxylic acids and salts thereof, carboxyl esters, thiols and thioethers; and $R_5$ is a further chain of amino acids, hydrogen, acetyl, or a protecting group.

16. The pharmaceutical composition of claim 1, wherein the proteasome inhibitor is represented by structural formula (III) or a pharmaceutically acceptable salt thereof

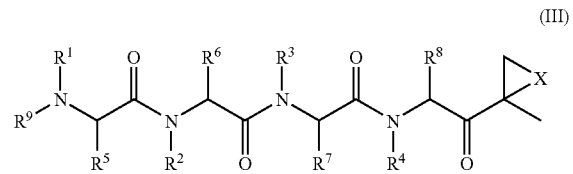

wherein:

X is O;

$R^1$, $R^2$, $R^3$, and $R^4$ are hydrogen $R^5$, $R^6$, $R^7$, and $R^8$ are independently selected from $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether; and $R^9$ is a further chain of amino acids, hydrogen, $C_{1-6}$acyl, a protecting group, aryl, or heteroaryl.

17. The pharmaceutical composition of claim 1, wherein the proteasome inhibitor is represented by structural formula (IV) or a pharmaceutically acceptable salt thereof:

(IV)

wherein:
X is O;
$R^1$, $R^2$, $R^3$ and $R^4$ are independently selected from hydrogen and a group of formula (IIIa), with the proviso that at least one of $R^1$, $R^2$, $R^3$, and $R^4$ is a group of formula (IIIa);
$R^6$ and $R^8$ independently are selected from $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof, carboxyl ester, thiol, and thioether;
$R^9$ is a further chain of amino acids, hydrogen, acyl, a protecting group, aryl, or heteroaryl.

18. The pharmaceutical composition of claim 1, wherein the proteasome inhibitor is represented by structural formula (V) or a pharmaceutically acceptable salt thereof:

(V)

wherein:
each A is independently selected from C=O, C=S, and $SO_2$;
L is absent or is selected from C=O, C=S, and $SO_2$;
M is absent or is $C_{1-8}$alkyl;
Q is absent or is selected from O, NH, and N—$C_{1-6}$alkyl;
X is O;
Y is absent or is selected from O, NH, N—$C_{1-6}$alkyl, S, SO, $SO_2$, $CHOR^{10}$, and $CHCO_2R^{10}$;
each Z is independently selected from O, S, NH, and N—$C_{1-6}$alkyl;
$R^1$, $R^2$, $R^3$, and $R^4$ are each independently selected from $C_{1-6}$alkyl, $C_{1-6}$hydroxyalkyl, $C_{1-6}$alkoxyalkyl, aryl, $C_{1-6}$aralkyl, heteroaryl, $C_{1-6}$heteroaralkyl, heterocyclyl, and $C_{1-6}$heterocycloalkyl, any of which is optionally substituted with one or more of amide, amine, carboxylic acid (or a salt thereof), ester, thiol, or thioether substituents;
$R^5$ is $N(R^6)LQR^7$;
$R^6$ is selected from hydrogen, OH, and $C_{1-6}$alkyl;
$R^7$ is selected from hydrogen, $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^8ZA$—$C_{1-8}$alkyl-, $R^{11}Z$—$C_{1-8}$alkyl-, $(R^8O)(R^9O)P(=O)O$—$C_{1-8}$alkyl-ZAZ—$C_{1-8}$alkyl-, $(R^8O)(R^9O)P(=O)O$—$C_{1-8}$alkyl-Z—$C_{1-8}$alkyl-, $R^8ZA$-$C_{1-8}$alkyl-ZAZ—$C_{1-8}$alkyl-, heterocyclylMZAZ—$C_{1-8}$alkyl-, $(R^8O)(R^9O)P(=O)O$—$C_{1-8}$alkyl-, $(R^{10})_2N$—$C_{1-8}$alkyl-, $(R^{10})_3N^+$—$C_{1-8}$alkyl-, heterocyclylM-, carbocyclylM-, $R^{11}SO_2C_{1-8}$alkyl-, and $R^{11}SO_2NH$; or
$R^6$ and $R^7$ together $C_{1-6}$alkyl-Y—$C_{1-6}$alkyl, $C_{1-6}$alkyl-ZA-$C_{1-6}$alkyl, A-$C_{1-6}$alkyl-ZA-$C_{1-6}$alkyl, A-$C_{1-6}$alkyl-A, or $C_{1-6}$alkyl-A, thereby forming a ring;
$R^8$ and $R^9$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, or $R^8$ and $R^9$ together are $C_{1-6}$alkyl, thereby forming a ring;
each $R^{10}$ is independently selected from hydrogen and $C_{1-6}$alkyl; and
$R^{11}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl,
provided that when $R_6$ is H, L is C=O, and Q is absent, $R^7$ is not hydrogen, $C_{1-6}$alkyl, or aryl or heteroaryl.

19. The pharmaceutical composition of claim 18, wherein the proteasome inhibitor is represented by structural formula (VI) or a pharmaceutically acceptable salt thereof:

(VI)

wherein:
each A is independently selected from C=O, C=S, and $SO_2$;
L is absent or is selected from C=O, C=S, and $SO_2$;
M is absent or is $C_{1-8}$alkyl;
Q is absent or is selected from O, NH, and N—$C_{1-6}$alkyl;
X is O;
Y is absent or is selected from O, NH, N—$C_{1-6}$alkyl, S, SO, $SO_2$, $CHOR^{10}$, and $CHCO_2R^{10}$;
each Z is independently selected from O, S, NH, and N—$C_{1-6}$alkyl;
$R^2$ and $R^4$ are each independently selected from $C_{1-6}$alkyl, $C_{1-6}$hydroxyalkyl, $C_{1-6}$alkoxyalkyl, aryl, and $C_{1-6}$aralkyl, any of which is optionally substituted with one or more of amide, amine, carboxylic acid or a salt thereof, ester, thiol, or thioether substituents;
$R^5$ is $N(R^6)LQR^7$;
$R^6$ is selected from hydrogen, OH, and $C_{1-6}$alkyl;
$R^7$ is selected from hydrogen, $C_{1-6}$alkyl, $C_{1-6}$alkenyl, $C_{1-6}$alkynyl, aryl, $C_{1-6}$aralkyl, heteroaryl, $C_{1-6}$heteroaralkyl, $R^8ZA$-$C_{1-8}$alkyl-, $R^{11}Z$—$C_{1-8}$alkyl-, $(R^8O)(R^9O)P(=O)O$—$C_{1-8}$alkyl-ZAZ—$C_{1-8}$alkyl-, $(R^8O)(R^9O)P(=O)O$—$C_{1-8}$alkyl-Z—$C_{1-8}$alkyl-, $R^8ZA$-$C_{1-8}$alkyl-ZAZ—$C_{1-8}$alkyl-, heterocyclylMZAZ—$C_{1-8}$alkyl-, $(R^8O)(R^9O)P(=O)O$—$C_{1-8}$alkyl-, $(R^{10})_2N$—$C_{1-8}$alkyl-, $(R^{10})_3N^+$—$C_{1-8}$alkyl-, heterocyclylM-, carbocyclylM-, $R^{11}SO_2C_{1-8}$alkyl-, and $R^{11}SO_2NH$; or $R^6$ and $R^7$ together are $C_{1-6}$alkyl-Y—$C_{1-6}$alkyl, $C_{1-6}$alkyl-ZA-$C_{1-6}$alkyl, A-$C_{1-6}$alkyl-ZA-$C_{1-6}$alkyl, A-$C_{1-6}$alkyl-A, or $C_{1-6}$alkyl-A, thereby forming a ring;

$R^8$ and $R^9$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, or $R^8$ and $R^9$ together are $C_{1-6}$alkyl, thereby forming a ring;

each $R^{10}$ is independently selected from hydrogen and $C_{1-6}$alkyl; and $R^{11}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

provided that when $R_6$ is H, L is C=O, and Q is absent, $R^7$ is not hydrogen, $C_{1-6}$alkyl, or aryl or heteroaryl.

20. The pharmaceutical composition of claim 19, wherein the proteasome inhibitor is represented by the following structural formula or a pharmaceutically acceptable salt thereof:

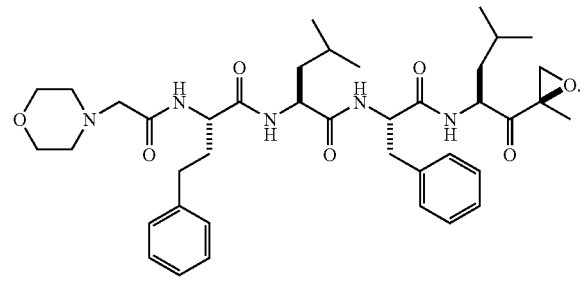

21. The pharmaceutical composition of claim 1, wherein the proteasome inhibitor is represented by structural formula (VII) or a pharmaceutically acceptable salt thereof:

(VII)

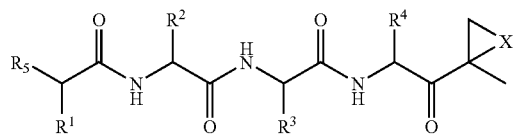

wherein:
each A is independently selected from C=O, C=S, and $SO_2$;
each B is independently selected from C=O, C=S, and $SO_2$;
D is absent or is $C_{1-8}$alkyl;
G is selected from O, NH, and N—$C_{1-6}$alkyl;
K is absent or is selected from C=O, C=S, and $SO_2$;
L is absent or is selected from C=O, C=S, and $SO_2$;
M is absent or is $C_{1-8}$alkyl;
Q is absent or is selected from O, NH, and N—$C_{1-6}$alkyl;
X is O;
each V is independently absent or is selected from O, S, NH, and N—$C_{1-6}$alkyl;
W is absent or is independently selected from O, S, NH, and N—$C_{1-6}$alkyl;
Y is absent or is selected from O, NH, N—$C_{1-6}$alkyl, S, SO, $SO_2$, $CHOR^{10}$, and $CHCO_2R^{10}$;
each Z is independently selected from O, S, NH, and N—$C_{1-6}$alkyl;
$R^1$, $R^2$, $R^3$, and $R^4$ are each independently selected from $C_{1-6}$alkyl, $C_{1-6}$hydroxyalkyl, $C_{1-6}$alkoxyalkyl, aryl, $C_{1-6}$aralkyl, heteroaryl, $C_{1-6}$heteroaralkyl, heterocyclyl, and $C_{1-6}$heterocycloalkyl, and $R^{14}DVKOC_{1-3}$alkyl-, wherein at least one of $R^1$ and $R^3$ is $R^{14}DVKOC_{1-3}$alkyl-;
$R^5$ is $N(R^6)LQR^7$;
$R^6$ is selected from hydrogen, OH, and $C_{1-6}$alkyl;

$R^7$ is a further chain of amino acids, hydrogen, a protecting group, aryl, or heteroaryl, any of which is optionally substituted with halogen, carbonyl, nitro, hydroxy, aryl, $C_{1-5}$alkyl; or $R^7$ is selected from $C_{1-6}$alkyl, $C_{1-6}$alkenyl, $C_{1-6}$alkynyl, $C_{1-6}$aralkyl, $C_{1-6}$heteroaralkyl, $R^8ZA$-$C_{1-8}$alkyl-, $R^{11}Z$—$C_{1-8}$alkyl-, $(R^8O)(R^9O)P(=O)O$—$C_{1-8}$alkyl-ZAZ—$C_{1-8}$alkyl-, $(R^8O)(R^9O)P(=O)O$—$C_{1-8}$alkyl-Z—$C_{1-8}$alkyl-, $R^8ZA$-$C_{1-8}$alkyl-ZAZ—$C_{1-8}$alkyl-, heterocyclylMZAZ—$C_{1-8}$alkyl-, $(R^8O)(R^9O)P(=O)O$—$C_{1-8}$alkyl-, $(R^{10})_2N$—$C_{1-8}$alkyl-, $(R^{10})_3N^+$—$C_{1-8}$alkyl-, heterocyclylM-, carbocyclylM-, $R^{11}SO_2C_{1-8}$alkyl-, and $R^{11}SO_2NH$; or $R^6$ and $R^7$ together are $C_{1-6}$alkyl-Y—$C_{1-6}$alkyl, $C_{1-6}$alkyl-ZA-$C_{1-6}$alkyl, A-$C_{1-6}$alkyl-ZA-$C_{1-6}$alkyl, A-$C_{1-6}$alkyl-A, or $C_{1-6}$alkyl-A, thereby forming a ring;

$R^8$ and $R^9$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, or $R^8$ and $R^9$ together are $C_{1-6}$alkyl, thereby forming a ring;

each $R^{10}$ is independently selected from hydrogen and $C_{1-6}$alkyl;

$R^{11}$ is independently selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

$R^{14}$ is selected from hydrogen, $(R^{15}O)(R^{16}O)P(=O)W$—, $R^{15}GB$—, heterocyclyl-, $(R^{17})_2N$—, $(R^{17})_3N^+$—, $R^{17}SO_2GBG$-, and $R^{15}GBC_{1-8}$alkyl- where the $C_{1-8}$alkyl moiety is optionally substituted with OH, $C_{1-8}$alkylW optionally substituted with halogen, aryl, heteroaryl, carbocyclyl, heterocyclyl, and $C_{1-6}$aralkyl;

$R^{15}$ and $R^{16}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, or $R^{15}$ and $R^{16}$ together are $C_{1-6}$alkyl, thereby forming a ring; and $R^{17}$ is selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and $C_{1-6}$heteroaralkyl;

provided that when $R_6$ is H, L is C=O, and Q is absent, $R^7$ is not hydrogen, $C_{1-6}$alkyl, or aryl or heteroaryl; and D, G, V, K, and W are selected such that there are no O—O, N—O, S—N, or S—O bonds.

22. The pharmaceutical composition of claim 21, wherein the proteasome inhibitor is represented by structural formula (VIII) or a pharmaceutically acceptable salt thereof:

(VIII)

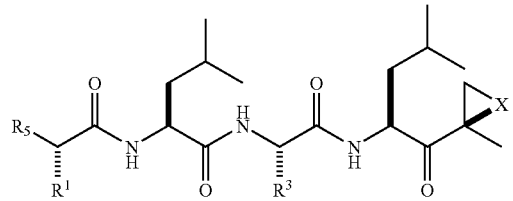

where:
each A is independently selected from C=O, C=S, and $SO_2$;
each B is independently selected from C=O, C=S, and $SO_2$;
D is absent or is $C_{1-8}$alkyl;
G is selected from O, NH, and N—$C_{1-6}$alkyl;
K is absent or is selected from C=O, C=S, and $SO_2$;
L is absent or is selected from C=O, C=S, and $SO_2$;
M is absent or is $C_{1-8}$alkyl;
Q is absent or is selected from O, NH, and N—$C_{1-6}$alkyl;
X is s O;
each V is independently absent or is selected from O, S, NH, and N—$C_{1-6}$alkyl;

W is absent or is independently selected from O, S, NH, and N—$C_{1-6}$alkyl;

Y is absent or is selected from O, NH, N—$C_{1-6}$alkyl, S, SO, $SO_2$, $CHOR^{10}$, and $CHCO_2R^{10}$;

each Z is independently selected from O, S, NH, and N—$C_{1-6}$alkyl;

$R^1$ and $R^3$ are each independently selected from $C_{1-6}$alkyl, $C_{1-6}$hydroxyalkyl, $C_{1-6}$alkoxyalkyl, aryl, $C_{1-6}$aralkyl, and $R^{14}DVKOC_{1-3}$alkyl-, wherein at least one of $R^1$ and $R^3$ is $R^{14}DVKOC_{1-3}$alkyl-;

$R^5$ is $N(R^6)LQR^7$;

$R^6$ is selected from hydrogen, OH, and $C_{1-6}$alkyl;

$R^7$ is a further chain of amino acids, hydrogen, a protecting group, aryl, or heteroaryl, any of which is optionally substituted with halogen, carbonyl, nitro, hydroxy, aryl, $C_{1-5}$alkyl; or $R^7$ is selected from $C_{1-6}$alkyl, $C_{1-6}$alkenyl, $C_{1-6}$alkynyl, $C_{1-6}$aralkyl, $C_{1-6}$heteroaralkyl, $R^8ZA$-$C_{1-8}$alkyl-, $R^{11}Z$—$C_{1-8}$alkyl-, $(R^8O)(R^9O)P(=O)O$—$C_{1-8}$alkyl-$ZAZ$—$C_{1-8}$alkyl-, $(R^8O)(R^9O)P(=O)O$—$C_{1-8}$alkyl-$Z$—$C_{1-8}$alkyl-, $R^8ZA$-$C_{1-8}$alkyl-$ZAZ$—$C_{1-8}$alkyl-, heterocyclyl$MZAZ$—$C_{1-8}$alkyl-, $(R^8O)(R^9O)P(=O)O$—$C_{1-8}$alkyl-, $(R^{10})_2N$—$C_{1-8}$alkyl-, $(R^{10})_3N^+$—$C_{1-8}$alkyl-, heterocyclyl$M$-, carbocyclyl$M$-, $R^{11}SO_2$ $C_{1-8}$alkyl-, and $R^{11}SO_2NH$; or $R^6$ and $R^7$ together are $C_{1-6}$alkyl-Y—$C_{1-6}$alkyl, $C_{1-6}$alkyl-$ZA$-$C_{1-6}$alkyl, A-$C_{1-6}$alkyl-$ZA$-$C_{1-8}$alkyl, A-$C_{1-6}$alkyl-A, or $C_{1-6}$alkyl-A, thereby forming a ring;

$R^8$ and $R^9$ are independently selected from hydrogen, metal cation, $C_{1-6}$alkyl, $C_{1-6}$alkenyl, $C_{1-6}$alkynyl, aryl, heteroaryl, $C_{1-6}$aralkyl, and $C_{1-6}$heteroaralkyl, or $R^8$ and $R^9$ together are $C_{1-6}$alkyl, thereby forming a ring;

each $R^{10}$ is independently selected from hydrogen and $C_{1-6}$alkyl; and $R^{11}$ is independently selected from hydrogen, $C_{1-6}$alkyl, $C_{1-6}$alkenyl, $C_{1-8}$alkynyl, carbocyclyl, heterocyclyl, aryl, heteroaryl, $C_{1-6}$aralkyl, and $C_{1-6}$heteroaralkyl, $R^{14}$ is selected from hydrogen, $(R^{15}O)(R^{16}O)P(=O)W$—, $R^{15}GB$—, heterocyclyl-, $(R^{17})_2N$—, $(R^{17})_3N^+$—, $R^{17}SO_2GBG$-, and $R^{15}GBC_{1-8}$alkyl- where the $C_{1-8}$alkyl moiety is optionally substituted with OH, $C_{1-8}$alkylW optionally substituted with halogen, aryl, heteroaryl, carbocyclyl, heterocyclyl, and $C_{1-6}$aralkyl;

$R^{15}$ and $R^{16}$ are independently selected from hydrogen, metal cation, $C_{1-6}$alkyl, $C_{1-6}$alkenyl, $C_{1-6}$alkynyl, aryl, heteroaryl, $C_{1-6}$aralkyl, $C_{1-6}$heteroaralkyl, or $R^{15}$ and $R^{16}$ together are $C_{1-6}$alkyl, thereby forming a ring;

$R^{17}$ is selected from hydrogen, $C_{1-6}$alkyl, $C_{1-6}$alkenyl, $C_{1-6}$alkynyl, carbocyclyl, heterocyclyl, aryl, heteroaryl, $C_{1-6}$aralkyl, and heteroaralkyl;

provided that when $R_6$ is H, L is C=O, and Q is absent, $R^7$ is not hydrogen, $C_{1-6}$alkyl, or aryl or heteroaryl; and D, G, V, K, and W are selected such that there are no O—O, N—O, S—N, or S—O bonds.

23. The pharmaceutical composition of claim 1, wherein the proteasome inhibitor is represented by structural formula (IX) or a pharmaceutically acceptable salt thereof:

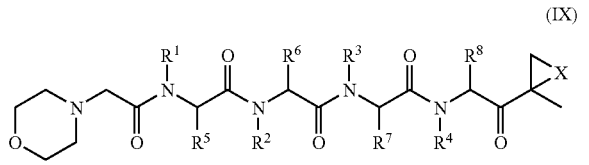

(IX)

wherein:

X is O;

$R^1$, $R^2$, $R^3$, and $R^4$ are hydrogen; and $R^5$, $R^6$, $R^7$, and $R^8$ are independently selected from H, $C_{1-6}$alkyl, $C_{1-6}$hydroxyalkyl, $C_{1-6}$alkoxyalkyl, aryl, $C_{1-6}$aralkyl, heteroaryl, $C_{1-6}$heteroaralkyl, heterocyclyl, and $C_{1-6}$heterocycloalkyl, each of which is optionally substituted with a group selected from amide, amine, carboxylic acid or a pharmaceutically acceptable salt thereof, carboxyl ester, thiol, and thioether.

24. The pharmaceutical composition of claim 23, wherein the proteasome inhibitor is represented by structural formula (X) or a pharmaceutically acceptable salt thereof:

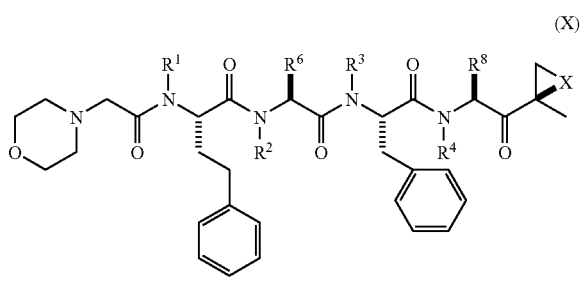

(X)

wherein:

X is O;

$R^1$, $R^2$, $R^3$, and $R^4$ are independently selected from hydrogen and a group of formula (IXa); and $R^6$ and $R^8$ are independently selected from H, $C_{1-6}$alkyl, $C_{1-6}$hydroxyalkyl, $C_{1-6}$alkoxyalkyl, aryl, and $C_{1-6}$aralkyl, each of which is optionally substituted with a group selected from amide, amine, carboxylic acid or a pharmaceutically acceptable salt thereof carboxyl ester, thiol, and thioether.

25. The pharmaceutical composition of claim 1, wherein the proteasome inhibitor is represented by structural formula (XI) or a pharmaceutically acceptable salt thereof:

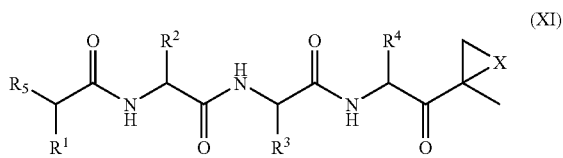

(XI)

wherein:

X is O;

$R^1$, $R^2$, $R^3$, and $R^4$ are each independently selected from $C_{1-6}$alkyl, $C_{1-6}$hydroxyalkyl, $C_{1-6}$alkoxyalkyl, aryl, $C_{1-6}$aralkyl, heteroaryl, $C_{1-6}$heteroaralkyl, heterocyclyl, and $C_{1-6}$heterocycloalkyl, any of which is optionally substituted with one or more of amide, amine, carboxylic acid, ester, thiol, or thioether substituents;

$R^5$ is $N(R^6)R^7$;

$R^6$ is selected from hydrogen, OH, and $C_{1-6}$alkyl; and $R^7$ comprises a detectable label.

26. The pharmaceutical composition of claim 25, wherein the proteasome inhibitor is represented by structural formula (XII) or a pharmaceutically acceptable salt thereof:

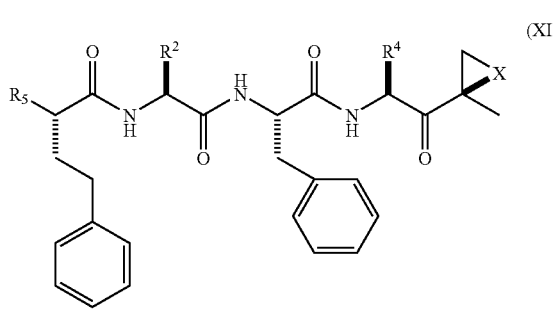

(XII)

wherein:
X is O;
R² and R⁴ are each independently selected from C$_{1-6}$alkyl, C$_{1-6}$hydroxyalkyl, C$_{1-6}$alkoxyalkyl, aryl, and C$_{1-6}$aralkyl, any of which is optionally substituted with one or more of amide, amine, carboxylic acid, ester, thiol, or thioether substituents;
R⁵ is N(R⁶)R⁷;
R⁶ is selected from hydrogen, OH, and C$_{1-6}$alkyl; and
R⁷ comprises a detectable label.

27. The pharmaceutical composition of claim 1, wherein the proteasome inhibitor is represented by structural formula (XIII) or (XIV) or a pharmaceutically acceptable salt thereof:

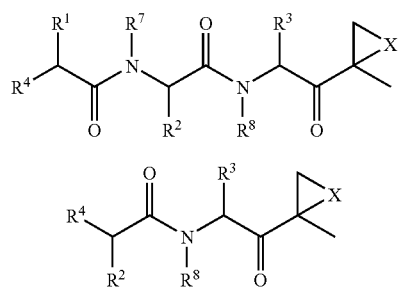

(XIII)

(XIV)

wherein:
each Ar is independently an aromatic or heteroaromatic group optionally substituted with 1 to 4 substituents;
L is selected from C=O, C=S, and SO₂;
X is s O;
Y is absent or is selected from C=O and SO₂;
Z is absent or is C$_{1-6}$alkyl;
R¹, R², and R³ are each independently selected from C$_{1-6}$alkyl, C$_{1-6}$hydroxyalkyl, C$_{1-6}$alkoxyalkyl, aryl, C$_{1-6}$aralkyl, heteroaryl, C$_{1-6}$heteroaralkyl, heterocyclyl, and C$_{1-6}$heterocycloalkyl, any of which is optionally substituted with one or more of amide, amine, carboxylic acid, ester, thiol, or thioether substituents;
R⁴ is N(R⁵)L-Z—R⁶;
R⁵ is selected from hydrogen, OH, C$_{1-6}$aralkyl, and C$_{1-6}$alkyl;
R⁶ is selected from hydrogen, C$_{1-6}$alkenyl, Ar—Y—, carbocyclyl, and heterocyclyl; and
R⁷ and R⁸ are independently selected from hydrogen, C$_{1-6}$alkyl, and C$_{1-6}$aralkyl.

28. The pharmaceutical composition of claim 27 wherein the proteasome inhibitor is represented by structural formula (XV) or (XVI) or a pharmaceutically acceptable salt thereof:

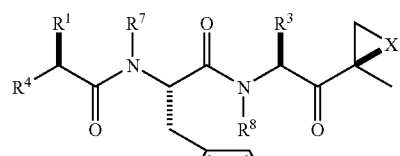

(XV)

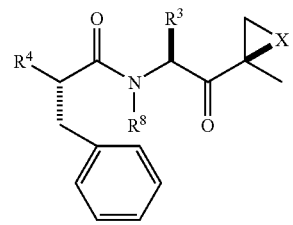

(XVI)

wherein:
each Ar is independently an aromatic or heteroaromatic group optionally substituted with 1-4 substituents;
L is selected from C=O, C=S, and SO₂;
X is O;
Y is absent or is selected from C=O and SO₂;
Z is absent or is C$_{1-6}$alkyl;
R¹ and R³ are each independently selected from C$_{1-6}$alkyl, C$_{1-6}$hydroxyalkyl, C$_{1-6}$alkoxyalkyl, aryl, and C$_{1-6}$aralkyl, any of which is optionally substituted with one or more of amide, amine, carboxylic acid, ester, thiol, or thioether substituents;
R⁴ is N(R⁵)L-Z—R⁶;
R⁵ is selected from hydrogen, OH, C$_{1-6}$aralkyl, and C$_{1-6}$alkyl;
R⁶ is selected from hydrogen, C$_{1-6}$alkenyl, Ar—Y—, carbocyclyl, and heterocyclyl; and
R⁷ and R⁸ are independently selected from hydrogen, C$_{1-6}$alkyl, and C$_{1-6}$aralkyl.

29. A pharmaceutical composition comprising a compound having a structure

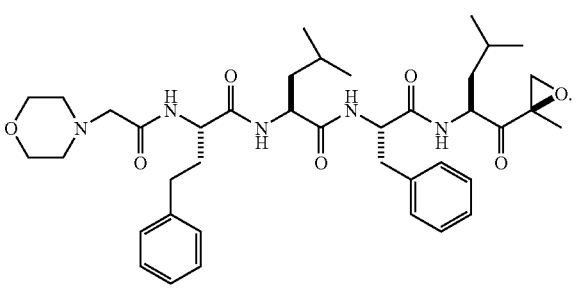

or a pharmaceutically acceptable salt thereof, and a substituted cyclodextrin selected from hydroxypropyl beta-cyclodextrin and sulfobutyl ether beta-cyclodextrin (SBECD).

30. A pharmaceutical composition of claim 29, wherein the cyclodextrin is SBECD.

31. A pharmaceutical composition comprising a compound having a structure
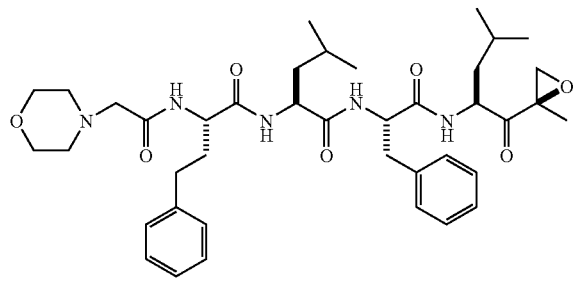
or a pharmaceutically acceptable salt thereof, in an aqueous solution containing 10% (w/v) SBECD and 10 mM citric acid adjusted to pH 3.5.
32. A pharmaceutical composition in the form of a lyophilisate comprising SBECD and a compound having a structure
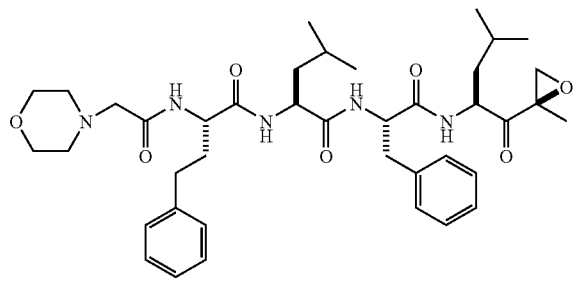
or a pharmaceutically acceptable salt thereof.
* * * * *

UNITED STATES PATENT AND TRADEMARK OFFICE
CERTIFICATE OF CORRECTION

PATENT NO. : 7,737,112 B2  Page 1 of 1
APPLICATION NO. : 11/299265
DATED : June 15, 2010
INVENTOR(S) : Lewis et al.

It is certified that error appears in the above-identified patent and that said Letters Patent is hereby corrected as shown below:

In claim 22, column 54, line 65, please replace "X is s O;" with --X is O;--;

In claim 22, column 55, line 26, please replace "A-$C_{1-6}$alkyl-ZA-$C_{1-8}$alkyl," with --A-$C_{1-6}$alkyl-ZA-$C_{1-6}$alkyl,--;

In claim 22, column 55, line 35, please replace "$C_{1-8}$alkynl," with --$C_{1-6}$alkynl,--;

In claim 22, column 55, line 49, please replace "and heteroaralkyl;" with --and $C_{1-6}$heteroaralkyl;--;

In claim 27, column 57, line 51, please replace "X is s O;" with --X is O;--.

Signed and Sealed this

Twenty-fourth Day of August, 2010

David J. Kappos
*Director of the United States Patent and Trademark Office*